United States Patent
Lamson et al.

(10) Patent No.: US 10,292,801 B2
(45) Date of Patent: May 21, 2019

(54) SYSTEM FOR DELIVERING ANCHORS FOR TREATING INCONTINENCE

(71) Applicant: Neotract, Inc, Pleasanton, CA (US)

(72) Inventors: Theodore C Lamson, Pleasanton, CA (US); Joseph Catanese, III, San Leandro, CA (US); Matthew McLean, San Francisco, CA (US); James W Niederjohn, San Jose, CA (US); Floria Cheng, San Francisco, CA (US); Brian Y Tachibana, Oakland, CA (US); Michael Gearhart, Fremont, CA (US)

(73) Assignee: NeoTract, Inc., Pleasanton, CA (US)

( * ) Notice: Subject to any disclaimer, the term of this patent is extended or adjusted under 35 U.S.C. 154(b) by 0 days.

(21) Appl. No.: 13/852,756

(22) Filed: Mar. 28, 2013

(65) Prior Publication Data

US 2013/0296639 A1    Nov. 7, 2013

Related U.S. Application Data

(60) Provisional application No. 61/617,244, filed on Mar. 29, 2012.

(51) Int. Cl.
*A61F 2/00* (2006.01)
*A61B 17/00* (2006.01)
(Continued)

(52) U.S. Cl.
CPC ........ *A61F 2/0022* (2013.01); *A61B 17/0401* (2013.01); *A61B 17/0218* (2013.01);
(Continued)

(58) Field of Classification Search
CPC ........ A61F 2/0811; A61F 2/04; A61F 2/0022; A61F 2/0036; A61F 2220/0016;
(Continued)

(56) References Cited

U.S. PATENT DOCUMENTS 659,422 A    10/1900   Shidler
780,392 A    1/1905    Wanamaker
(Continued)

FOREIGN PATENT DOCUMENTS

CA    2477220      11/2007
CN    1697633 A    11/2005
(Continued)

OTHER PUBLICATIONS

Berges, Richard, "Alternative Minimalinvasive Therapien Beim Benignen Prostatasyndrom", medizin, Jg, 104 heft 37, (Sep. 2007), 12 pgs.
(Continued)

*Primary Examiner* — Kaylee R Wilson
(74) *Attorney, Agent, or Firm* — Christopher J. Buchko

(57) ABSTRACT

A system and associated method for manipulating tissues and anatomical or other structures in medical applications for the purpose of treating incontinence. In one aspect, the system includes a delivery device configured to deploy and implant anchor devices for distracting and/or retracting the urethra or tissues proximate thereto, or to maintain a position of a urethra in response to intra-abdominal pressures.

12 Claims, 12 Drawing Sheets

(51) Int. Cl.
*A61B 17/04* (2006.01)
*A61B 17/02* (2006.01)
*A61B 17/06* (2006.01)

(52) U.S. Cl.
CPC .............. *A61B 2017/00274* (2013.01); *A61B 2017/00805* (2013.01); *A61B 2017/00893* (2013.01); *A61B 2017/0409* (2013.01); *A61B 2017/0419* (2013.01); *A61B 2017/06052* (2013.01); *A61F 2/0036* (2013.01)

(58) Field of Classification Search
CPC ...... A61F 2220/0033; A61F 2220/0075; A61F 2220/0025; A61F 2220/0091; A61F 2220/0008; A61F 2002/0829; A61F 2002/0823; A61B 2017/00805; A61B 2017/0417; A61B 2017/00274; A61B 2017/00893; A61B 2017/0409; A61B 2017/064; A61B 2017/0464; A61B 2017/0419; A61B 2017/06057; A61B 17/0401; A61B 17/064; A61B 17/07292; A61B 17/0218
USPC ..................................... 600/30, 37; 606/151
See application file for complete search history.

(56) References Cited

U.S. PATENT DOCUMENTS

| | | |
|---|---|---|
| 789,467 A | 5/1905 | West |
| 2,360,164 A | 10/1944 | Frank |
| 2,485,531 A | 10/1949 | William |
| 2,579,192 A | 12/1951 | Kohl |
| 2,646,298 A | 7/1953 | Leary |
| 2,697,624 A | 12/1954 | Thomas |
| 2,734,299 A | 2/1956 | Masson |
| 2,825,592 A | 3/1958 | McKenzie |
| 3,326,586 A | 6/1967 | Frost |
| 3,470,834 A | 10/1969 | Bone |
| 3,521,918 A | 7/1970 | Hammond |
| 3,541,591 A | 11/1970 | Hoegerman |
| 3,664,345 A | 5/1972 | Dabbs |
| 3,713,680 A | 1/1973 | Pagano |
| 3,716,058 A | 2/1973 | Tanner |
| 3,756,638 A | 9/1973 | Stockberger |
| 3,873,140 A | 3/1975 | Bloch |
| 3,875,648 A | 4/1975 | Bone |
| 3,886,933 A | 6/1975 | Mori |
| 3,931,667 A | 1/1976 | Merser |
| 3,976,079 A | 8/1976 | Samuels |
| 4,006,747 A | 2/1977 | Kronenthal |
| 4,137,920 A | 2/1979 | Bonnet |
| 4,164,225 A | 8/1979 | Johnson |
| 4,210,148 A | 7/1980 | Stivala |
| 4,235,238 A | 11/1980 | Ogiu |
| 4,291,698 A | 9/1981 | Fuchs |
| 4,409,974 A | 10/1983 | Freedland |
| 4,419,094 A | 12/1983 | Patel |
| 4,452,236 A | 6/1984 | Utsugi |
| 4,493,323 A | 1/1985 | Albright |
| 4,513,746 A | 4/1985 | Aranyi |
| 4,621,640 A | 11/1986 | Mulhollan |
| 4,655,771 A | 4/1987 | Wallsten |
| 4,657,461 A | 4/1987 | Smith |
| 4,669,473 A | 6/1987 | Richards |
| 4,705,040 A | 11/1987 | Mueller |
| 4,714,281 A | 12/1987 | Peck |
| 4,738,255 A | 4/1988 | Goble |
| 4,741,330 A | 5/1988 | Hayhurst |
| 4,744,364 A | 5/1988 | Kensey |
| 4,750,492 A | 6/1988 | Jacobs |
| 4,762,128 A | 8/1988 | Rosenbluth |
| 4,823,794 A | 4/1989 | Pierce |
| 4,863,439 A | 9/1989 | Sanderson |
| 4,893,623 A | 1/1990 | Rosenbluth |
| 4,899,743 A | 2/1990 | Nicholson |
| 4,926,860 A | 5/1990 | Stice |
| 4,935,028 A | 6/1990 | Drews |
| 4,946,468 A | 8/1990 | Li |
| 4,955,859 A | 9/1990 | Zilber |
| 4,955,913 A | 9/1990 | Robinson |
| 4,968,315 A | 11/1990 | Gatturna |
| 5,002,550 A | 3/1991 | Li |
| 5,019,032 A | 5/1991 | Robertson |
| 5,041,129 A | 8/1991 | Hayhurst |
| 5,046,513 A | 9/1991 | Gatturna |
| 5,053,046 A | 10/1991 | Janese |
| 5,078,731 A | 1/1992 | Hayhurst |
| 5,080,660 A | 1/1992 | Buelna |
| 5,098,374 A | 3/1992 | Othel-Jacobsen |
| 5,100,421 A | 3/1992 | Christoudias |
| 5,123,914 A | 6/1992 | Cope |
| 5,127,393 A | 7/1992 | McFarlin |
| 5,129,912 A | 7/1992 | Noda |
| 5,133,713 A | 7/1992 | Chu |
| 5,159,925 A | 11/1992 | Neuwirth |
| 5,160,339 A | 11/1992 | Chen |
| 5,163,960 A | 11/1992 | Bonutti |
| 5,167,614 A | 12/1992 | Tessmann et al. |
| 5,192,303 A | 3/1993 | Gatturna |
| 5,203,787 A | 4/1993 | Noblitt |
| 5,207,672 A | 5/1993 | Roth |
| 5,217,470 A | 6/1993 | Weston |
| 5,217,486 A | 6/1993 | Rice |
| 5,234,454 A | 8/1993 | Bangs |
| 5,236,445 A | 8/1993 | Hayhurst |
| 5,237,984 A | 8/1993 | Williams |
| 5,254,126 A | 10/1993 | Filipi et al. |
| 5,258,015 A | 11/1993 | Li |
| 5,267,960 A | 12/1993 | Hayman |
| 5,269,802 A | 12/1993 | Garber |
| 5,269,809 A | 12/1993 | Hayhurst |
| 5,300,099 A | 4/1994 | Rudie |
| 5,306,280 A | 4/1994 | Bregen et al. |
| 5,322,501 A | 6/1994 | Mahmud-Durrani |
| 5,330,488 A | 7/1994 | Goldrath |
| 5,334,200 A | 8/1994 | Johnson |
| 5,336,240 A | 8/1994 | Metzler |
| 5,350,399 A | 9/1994 | Erlebacher et al. |
| 5,354,271 A | 10/1994 | Voda |
| 5,358,511 A | 10/1994 | Gatturna |
| 5,364,408 A | 11/1994 | Gordon |
| 5,366,490 A | 11/1994 | Edwards |
| 5,368,599 A | 11/1994 | Hirsch |
| 5,370,646 A | 12/1994 | Reese |
| 5,370,661 A | 12/1994 | Branch |
| 5,372,600 A | 12/1994 | Beyar et al. |
| 5,380,334 A | 1/1995 | Torrie |
| 5,391,182 A | 2/1995 | Chin |
| 5,403,348 A | 4/1995 | Bonutti |
| 5,405,352 A | 4/1995 | Weston |
| 5,409,453 A | 4/1995 | Lundquist et al. |
| 5,411,520 A | 5/1995 | Nash |
| 5,417,691 A | 5/1995 | Hayhurst |
| 5,435,805 A | 7/1995 | Edwards |
| 5,458,612 A | 10/1995 | Chin |
| 5,464,416 A | 11/1995 | Steckel |
| 5,470,308 A | 11/1995 | Edwards et al. |
| 5,470,337 A | 11/1995 | Moss |
| 5,472,446 A | 12/1995 | de la Torre |
| 5,480,406 A | 1/1996 | Nolan |
| 5,499,994 A | 3/1996 | Tihon |
| 5,501,690 A | 3/1996 | Measamer |
| 5,507,754 A | 4/1996 | Green |
| 5,522,846 A | 6/1996 | Bonutti |
| 5,531,759 A | 7/1996 | Kensey et al. |
| 5,531,763 A | 7/1996 | Mastri |
| 5,534,012 A | 7/1996 | Bonutti |
| 5,536,240 A | 7/1996 | Edwards |
| 5,540,655 A | 7/1996 | Edwards et al. |
| 5,540,704 A | 7/1996 | Gordon |
| 5,542,594 A | 8/1996 | McKean et al. |
| 5,545,171 A | 8/1996 | Sharkey |
| 5,545,178 A | 8/1996 | Kensey |

(56) References Cited

U.S. PATENT DOCUMENTS

| | | |
|---|---|---|
| 5,549,631 A | 8/1996 | Bonutti |
| 5,550,172 A | 8/1996 | Regula |
| 5,554,162 A | 9/1996 | DeLange |
| 5,554,171 A | 9/1996 | Gatturna |
| 5,562,688 A | 10/1996 | Riza |
| 5,562,689 A | 10/1996 | Green |
| 5,569,305 A | 10/1996 | Bonutti |
| 5,571,104 A | 11/1996 | Li |
| 5,573,540 A | 11/1996 | Yoon |
| 5,578,044 A | 11/1996 | Gordon |
| 5,591,177 A | 1/1997 | Lehrer |
| 5,591,179 A | 1/1997 | Edelstein |
| 5,593,421 A | 1/1997 | Bauer |
| 5,611,515 A | 3/1997 | Benderev |
| 5,620,461 A | 4/1997 | Moer et al. |
| 5,626,614 A | 5/1997 | Hart |
| 5,630,824 A | 5/1997 | Hart |
| 5,643,321 A | 7/1997 | McDevitt |
| 5,647,836 A | 7/1997 | Blake |
| 5,653,373 A | 8/1997 | Green et al. |
| 5,665,109 A | 9/1997 | Yoon |
| 5,667,486 A | 9/1997 | Mikulich |
| 5,667,488 A | 9/1997 | Lundquist |
| 5,667,522 A | 9/1997 | Flomenblit et al. |
| 5,669,917 A | 9/1997 | Sauer |
| 5,672,171 A | 9/1997 | Andrus et al. |
| 5,690,649 A | 11/1997 | Li |
| 5,690,677 A | 11/1997 | Schmieding |
| 5,697,950 A | 12/1997 | Fucci |
| 5,707,394 A | 1/1998 | Miller |
| 5,716,368 A | 2/1998 | de la Torre |
| 5,718,717 A | 2/1998 | Bonutti |
| 5,725,556 A | 3/1998 | Moser |
| 5,725,557 A | 3/1998 | Gatturna |
| 5,733,306 A | 3/1998 | Bonutti |
| 5,741,276 A | 4/1998 | Poloyko |
| 5,746,753 A | 5/1998 | Sullivan |
| 5,749,846 A | 5/1998 | Edwards |
| 5,749,889 A | 5/1998 | Bacich |
| 5,752,963 A | 5/1998 | Allard |
| 5,775,328 A | 7/1998 | Lowe et al. |
| 5,782,862 A | 7/1998 | Bonutti |
| 5,782,864 A | 7/1998 | Lizardi |
| 5,791,022 A | 8/1998 | Bohman |
| 5,800,445 A | 9/1998 | Ratcliff |
| 5,807,403 A | 9/1998 | Beyar |
| 5,810,848 A | 9/1998 | Hayhurst |
| 5,810,853 A | 9/1998 | Yoon |
| 5,814,072 A | 9/1998 | Bonutti |
| 5,830,179 A | 11/1998 | Mikus |
| 5,830,221 A | 11/1998 | Stein |
| 5,845,645 A | 12/1998 | Bonutti |
| 5,846,254 A | 12/1998 | Schulze |
| 5,861,002 A | 1/1999 | Desai |
| 5,868,762 A | 2/1999 | Cragg |
| 5,873,891 A | 2/1999 | Sohn |
| 5,879,357 A | 3/1999 | Heaton |
| 5,897,574 A | 4/1999 | Bonutti |
| 5,899,911 A | 5/1999 | Carter |
| 5,899,921 A | 5/1999 | Caspari |
| 5,904,679 A | 5/1999 | Clayman |
| 5,904,696 A | 5/1999 | Rosenman |
| 5,908,428 A | 6/1999 | Scirica |
| 5,908,447 A | 6/1999 | Schroeppel |
| 5,919,198 A | 7/1999 | Graves |
| 5,919,202 A | 7/1999 | Yoon |
| 5,921,982 A | 7/1999 | Lesh |
| 5,921,986 A | 7/1999 | Bonutti |
| 5,928,252 A | 7/1999 | Steadman |
| 5,931,844 A | 8/1999 | Thompson |
| 5,941,439 A | 8/1999 | Kammerer et al. |
| 5,944,739 A | 8/1999 | Zlock |
| 5,948,000 A | 9/1999 | Larsen et al. |
| 5,948,001 A | 9/1999 | Larsen |
| 5,948,002 A | 9/1999 | Bonutti |
| 5,954,057 A | 9/1999 | Li |
| 5,954,747 A | 9/1999 | Clark |
| 5,964,732 A | 10/1999 | Willard |
| 5,971,447 A | 10/1999 | Steck |
| 5,971,967 A | 10/1999 | Willard |
| 6,010,514 A | 1/2000 | Burney |
| 6,011,525 A | 1/2000 | Piole |
| 6,015,428 A | 1/2000 | Pagedas |
| 6,024,751 A | 2/2000 | Lovato et al. |
| 6,030,393 A | 2/2000 | Corlew |
| 6,033,413 A | 3/2000 | Mikus |
| 6,033,430 A | 3/2000 | Bonutti |
| 6,036,701 A | 3/2000 | Rosenman |
| 6,048,351 A | 4/2000 | Gordon |
| 6,053,908 A | 4/2000 | Crainich |
| 6,053,935 A | 4/2000 | Brenneman et al. |
| 6,056,722 A | 5/2000 | Jayaraman |
| 6,056,772 A | 5/2000 | Bonutti |
| 6,066,160 A | 5/2000 | Colvin |
| 6,068,648 A | 5/2000 | Cole |
| 6,080,167 A | 6/2000 | Lyell |
| 6,086,608 A | 7/2000 | Ek |
| 6,110,183 A | 8/2000 | Cope |
| 6,117,133 A | 9/2000 | Zappala |
| 6,117,160 A | 9/2000 | Bonutti |
| 6,117,161 A | 9/2000 | Li |
| 6,120,539 A | 9/2000 | Eldridge |
| 6,132,438 A | 10/2000 | Fleischman |
| 6,139,555 A | 10/2000 | Hart |
| RE36,974 E | 11/2000 | Bonutti |
| 6,143,006 A | 11/2000 | Chan |
| 6,152,935 A | 11/2000 | Kammerer |
| 6,156,044 A | 12/2000 | Kammerer |
| 6,156,049 A | 12/2000 | Lovato et al. |
| 6,159,207 A | 12/2000 | Yoon |
| 6,159,234 A | 12/2000 | Bonutti |
| 6,193,714 B1 | 2/2001 | McGaffigan et al. |
| 6,200,329 B1 | 3/2001 | Fung |
| 6,203,565 B1 | 3/2001 | Bonutti et al. |
| 6,206,895 B1 | 3/2001 | Levinson |
| 6,206,907 B1 | 3/2001 | Marino |
| 6,228,096 B1 | 5/2001 | Marchand |
| 6,235,024 B1 | 5/2001 | Tu |
| 6,258,124 B1 | 7/2001 | Darois |
| 6,261,302 B1 | 7/2001 | Voegele |
| 6,261,320 B1 | 7/2001 | Tam et al. |
| 6,270,530 B1 | 8/2001 | Eldridge |
| 6,280,441 B1 | 8/2001 | Ryan |
| 6,280,460 B1 | 8/2001 | Bolduc |
| 6,287,317 B1 | 9/2001 | Makower |
| 6,290,711 B1 | 9/2001 | Caspari |
| 6,306,158 B1 | 10/2001 | Bartlett |
| 6,312,448 B1 | 11/2001 | Bonutti |
| 6,319,263 B1 | 11/2001 | Levinson |
| 6,322,112 B1 | 11/2001 | Duncan |
| 6,332,889 B1 | 12/2001 | Sancoff |
| 6,382,214 B1 | 5/2002 | Raz et al. |
| 6,387,041 B1 | 5/2002 | Harari et al. |
| 6,398,795 B1 | 6/2002 | McAlister |
| 6,398,796 B2 | 6/2002 | Levinson |
| 6,425,900 B1 | 7/2002 | Knodel |
| 6,425,919 B1 | 7/2002 | Lambrecht |
| 6,428,538 B1 | 8/2002 | Blewett et al. |
| 6,428,562 B2 | 8/2002 | Bonutti |
| 6,436,107 B1 | 8/2002 | Wang |
| 6,461,355 B2 | 10/2002 | Svejkovsky |
| 6,482,235 B1 | 11/2002 | Lambrecht |
| 6,488,691 B1 | 12/2002 | Carroll |
| 6,491,672 B2 | 12/2002 | Slepian et al. |
| 6,491,707 B2 | 12/2002 | Makower |
| 6,494,888 B1 | 12/2002 | Cruz |
| 6,500,184 B1 | 12/2002 | Chan |
| 6,500,195 B2 | 12/2002 | Bonutti |
| 6,506,190 B1 | 1/2003 | Walshe |
| 6,506,196 B1 | 1/2003 | Laufer |
| 6,514,247 B1 | 2/2003 | McGaffigan et al. |
| 6,517,569 B2 | 2/2003 | Mikus |
| 6,527,702 B2 | 3/2003 | Whalen |
| 6,527,794 B1 | 3/2003 | McDevitt |

(56) References Cited

U.S. PATENT DOCUMENTS

| | | |
|---|---|---|
| 6,530,932 B1 | 3/2003 | Swayze |
| 6,533,796 B1 | 3/2003 | Sauer |
| 6,544,230 B1 | 4/2003 | Flaherty |
| 6,547,725 B1 | 4/2003 | Paolitto |
| 6,551,328 B2 | 4/2003 | Kortenbach |
| 6,551,333 B2 | 4/2003 | Kuhns |
| 6,565,578 B1 | 5/2003 | Peifer |
| 6,569,187 B1 | 5/2003 | Bonutti |
| 6,572,626 B1 | 6/2003 | Knodel |
| 6,572,635 B1 | 6/2003 | Bonutti |
| 6,572,653 B1 | 6/2003 | Simonson |
| 6,582,453 B1 | 6/2003 | Tran |
| 6,592,609 B1 | 7/2003 | Bonutti |
| 6,595,911 B2 | 7/2003 | LoVuolo |
| 6,596,013 B2 | 7/2003 | Yang |
| 6,599,311 B1 | 7/2003 | Biggs |
| 6,626,913 B1 | 9/2003 | McKinnon |
| 6,626,916 B1 | 9/2003 | Yeung |
| 6,626,919 B1 | 9/2003 | Swanstrom |
| 6,629,534 B1 | 10/2003 | St. Goar |
| 6,638,275 B1 | 10/2003 | McGaffigan et al. |
| 6,641,524 B2 | 11/2003 | Kovac |
| 6,641,592 B1 | 11/2003 | Sauer |
| 6,656,182 B1 | 12/2003 | Hayhurst |
| 6,660,008 B1 | 12/2003 | Foerster |
| 6,660,023 B2 | 12/2003 | McDevitt |
| 6,663,589 B1 | 12/2003 | Halevy |
| 6,663,633 B1 | 12/2003 | Pierson |
| 6,663,639 B1 | 12/2003 | Laufer |
| 6,699,263 B2 | 3/2004 | Cope |
| 6,702,846 B2 | 3/2004 | Mikus |
| 6,706,047 B2 | 3/2004 | Trout |
| 6,709,493 B2 | 3/2004 | DeGuiseppi |
| 6,715,804 B2 | 4/2004 | Beers |
| 6,719,709 B2 | 4/2004 | Whalen |
| 6,730,112 B2 | 5/2004 | Levinson |
| 6,736,823 B2 | 5/2004 | Darois |
| 6,736,854 B2 | 5/2004 | Vadurro |
| 6,740,098 B2 | 5/2004 | Abrams |
| 6,767,037 B2 | 7/2004 | Wenstrom |
| 6,770,076 B2 | 8/2004 | Foerster |
| 6,773,438 B1 | 8/2004 | Knodel |
| 6,773,441 B1 | 8/2004 | Laufer |
| 6,790,213 B2 | 9/2004 | Cherok |
| 6,790,223 B2 | 9/2004 | Reever |
| 6,802,838 B2 | 10/2004 | Loeb et al. |
| 6,802,846 B2 | 10/2004 | Hauschild |
| 6,821,282 B2 | 11/2004 | Perry |
| 6,821,285 B2 | 11/2004 | Laufer |
| 6,821,291 B2 | 11/2004 | Bolea |
| 6,835,200 B2 | 12/2004 | Laufer |
| 6,905,475 B2 | 6/2005 | Hauschild |
| 6,908,473 B2 | 6/2005 | Skiba |
| 6,921,361 B2 | 7/2005 | Suzuki |
| 6,926,732 B2 | 8/2005 | Derus |
| 6,951,565 B2 | 10/2005 | Keane |
| 6,986,775 B2 | 1/2006 | Morales |
| 6,986,784 B1 | 1/2006 | Weiser |
| 6,988,983 B2 | 1/2006 | Connors et al. |
| 6,991,596 B2 | 1/2006 | Whalen |
| 6,991,647 B2 | 1/2006 | Jadhav |
| 6,997,940 B2 | 2/2006 | Bonutti |
| 7,001,327 B2 | 2/2006 | Whalen |
| 7,004,965 B2 | 2/2006 | Gross |
| 7,008,381 B2 | 3/2006 | Janssens |
| 7,011,688 B2 | 3/2006 | Gryska |
| 7,015,253 B2 | 3/2006 | Escandon |
| 7,041,111 B2 | 5/2006 | Chu |
| 7,048,698 B2 | 5/2006 | Whalen |
| 7,048,747 B2 | 5/2006 | Arcia |
| 7,060,077 B2 | 6/2006 | Gordon |
| 7,063,715 B2 | 6/2006 | Onuki |
| 7,065,325 B2 | 6/2006 | Zegelin et al. |
| 7,081,126 B2 | 7/2006 | McDevitt |
| 7,083,638 B2 | 8/2006 | Foerster |
| 7,087,073 B2 | 8/2006 | Bonutti |
| 7,089,064 B2 | 8/2006 | Manker |
| 7,090,690 B2 | 8/2006 | Foerster et al. |
| 7,093,601 B2 | 8/2006 | Manker |
| 7,096,301 B2 | 8/2006 | Beaudoin |
| 7,104,949 B2 | 9/2006 | Anderson et al. |
| 7,105,004 B2 | 9/2006 | DiCesare |
| 7,108,655 B2 | 9/2006 | Whalen |
| 7,141,038 B2 | 11/2006 | Whalen |
| 7,153,314 B2 | 12/2006 | Laufer |
| 7,179,225 B2 | 2/2007 | Shluzas |
| 7,226,558 B2 | 6/2007 | Nieman |
| 7,232,448 B2 | 6/2007 | Battles |
| 7,255,675 B2 | 8/2007 | Gertner |
| 7,261,709 B2 | 8/2007 | Swoyer et al. |
| 7,261,710 B2 | 8/2007 | Elmouelhi et al. |
| 7,282,020 B2 | 10/2007 | Kaplan |
| 7,288,063 B2 | 10/2007 | Petros |
| 7,303,108 B2 | 12/2007 | Shelton |
| 7,320,701 B2 | 1/2008 | Haut |
| 7,322,974 B2 | 1/2008 | Swoyer |
| 7,326,221 B2 | 2/2008 | Sakamoto |
| 7,334,822 B1 | 2/2008 | Hines |
| 7,335,197 B2 | 2/2008 | Sage et al. |
| 7,340,300 B2 | 3/2008 | Christopherson |
| 7,399,304 B2 | 7/2008 | Gambale |
| 7,402,166 B2 | 7/2008 | Feigl |
| 7,416,554 B2 | 8/2008 | Lam |
| 7,417,175 B2 | 8/2008 | Oda |
| 7,437,194 B2 | 10/2008 | Skwarek et al. |
| 7,463,934 B2 | 12/2008 | Tronnes et al. |
| 7,470,228 B2 | 12/2008 | Connors et al. |
| 7,481,771 B2 | 1/2009 | Fonseca |
| 7,485,124 B2 | 2/2009 | Kuhns et al. |
| 7,553,317 B2 | 6/2009 | Weisenburgh |
| 7,608,108 B2 | 10/2009 | Bhatnagar |
| 7,632,297 B2 | 12/2009 | Gross |
| 7,645,286 B2 | 1/2010 | Catanese |
| 7,658,311 B2 | 2/2010 | Boudreaux |
| 7,666,197 B2 | 2/2010 | Orban |
| 7,674,275 B2 | 3/2010 | Martin |
| 7,682,374 B2 | 3/2010 | Foerster et al. |
| 7,695,494 B2 | 4/2010 | Foerster |
| 7,704,261 B2 | 4/2010 | Sakamoto |
| 7,727,248 B2 | 6/2010 | Smith |
| 7,731,725 B2 | 6/2010 | Gadberry et al. |
| 7,736,374 B2 | 6/2010 | Vaughan |
| 7,758,594 B2 | 7/2010 | Lamson |
| 7,766,923 B2 | 8/2010 | Catanese |
| 7,766,939 B2 | 8/2010 | Yeung et al. |
| 7,780,682 B2 | 8/2010 | Catanese et al. |
| 7,815,655 B2 | 10/2010 | Catanese et al. |
| 7,850,712 B2 | 12/2010 | Conlon et al. |
| 7,862,584 B2 | 1/2011 | Lyons et al. |
| 7,887,551 B2 | 2/2011 | Bojarski et al. |
| 7,896,891 B2 | 3/2011 | Catanese |
| 7,905,889 B2 | 3/2011 | Catanese |
| 7,905,904 B2 | 3/2011 | Stone et al. |
| 7,909,836 B2 | 3/2011 | McLean et al. |
| 7,914,542 B2 | 3/2011 | Lamson |
| 7,922,645 B2 | 4/2011 | Kaplan |
| 7,951,158 B2 | 5/2011 | Catanese et al. |
| 8,007,503 B2 | 8/2011 | Catanese |
| 8,043,309 B2 | 10/2011 | Catanese |
| 8,114,070 B2 | 2/2012 | Rubinsky et al. |
| 8,145,321 B2 | 3/2012 | Gross |
| 8,152,804 B2 | 4/2012 | Elmouelhi et al. |
| 8,157,815 B2 | 4/2012 | Catanese |
| 8,162,960 B2 | 4/2012 | Manzo |
| 8,167,830 B2 | 5/2012 | Noriega |
| 8,211,118 B2 | 7/2012 | Catanese et al. |
| 8,216,254 B2 | 7/2012 | McLean |
| 8,236,011 B2 | 8/2012 | Harris et al. |
| 8,251,985 B2 | 8/2012 | Hoey et al. |
| 8,273,079 B2 | 9/2012 | Hoey et al. |
| 8,298,132 B2 | 10/2012 | Connors et al. |
| 8,303,604 B2 | 11/2012 | Stone et al. |
| 8,308,765 B2 | 11/2012 | Saadat et al. |
| 8,333,776 B2 | 12/2012 | Cheng |

(56) References Cited

U.S. PATENT DOCUMENTS

| | | |
|---|---|---|
| 8,343,187 B2 | 1/2013 | Lamson et al. |
| 8,361,112 B2 | 1/2013 | Kempton et al. |
| 8,372,065 B2 | 2/2013 | Hoey et al. |
| 8,388,611 B2 | 3/2013 | Shadduck et al. |
| 8,388,653 B2 | 3/2013 | Nobis et al. |
| 8,394,110 B2 | 3/2013 | Catanese et al. |
| 8,394,113 B2 | 3/2013 | Wei |
| 8,419,723 B2 | 4/2013 | Shadduck et al. |
| 8,425,535 B2 | 4/2013 | McLean |
| 8,444,657 B2 | 5/2013 | Saadat et al. |
| 8,454,655 B2 | 6/2013 | Yeung et al. |
| 8,465,551 B1 | 6/2013 | Wijay et al. |
| 8,480,686 B2 | 7/2013 | Bakos et al. |
| 8,491,606 B2 | 7/2013 | Tong |
| 8,496,684 B2 | 7/2013 | Crainich et al. |
| 8,521,257 B2 | 8/2013 | Whitcomb et al. |
| 8,529,584 B2 | 9/2013 | Catanese et al. |
| 8,529,588 B2 | 9/2013 | Ahlberg et al. |
| 8,562,646 B2 | 10/2013 | Gellman et al. |
| 8,585,692 B2 | 11/2013 | Shadduck et al. |
| 8,603,106 B2 | 12/2013 | Catanese et al. |
| 8,603,123 B2 | 12/2013 | Todd |
| 8,603,187 B2 | 12/2013 | Kilemnick et al. |
| 8,628,542 B2 | 1/2014 | Merrick |
| 8,663,243 B2 | 3/2014 | Lamson et al. |
| 8,668,705 B2 | 3/2014 | Johnston et al. |
| 8,683,895 B2 | 4/2014 | Nash |
| 8,715,239 B2 | 5/2014 | Lamson et al. |
| 8,715,298 B2 | 5/2014 | Catanese et al. |
| 8,734,469 B2 | 5/2014 | Pribanic et al. |
| 8,790,356 B2 | 7/2014 | Darois et al. |
| 8,801,702 B2 | 8/2014 | Hoey et al. |
| 8,808,363 B2 | 8/2014 | Perry et al. |
| 8,814,856 B2 | 8/2014 | Elmouelhi et al. |
| 8,828,035 B2 | 9/2014 | Kim |
| 8,834,458 B2 | 9/2014 | Neuberger et al. |
| 8,880,195 B2 | 11/2014 | Azure |
| 8,900,293 B2 | 12/2014 | Forbes et al. |
| 8,920,437 B2 | 12/2014 | Harris et al. |
| 8,926,494 B1 | 1/2015 | Cook et al. |
| 8,945,114 B2 | 2/2015 | Elmouelhi et al. |
| 9,034,001 B2 | 5/2015 | Cheng et al. |
| 9,039,740 B2 | 5/2015 | Wales et al. |
| 9,089,320 B2 | 7/2015 | Spivey et al. |
| 9,150,817 B2 | 10/2015 | Furihata et al. |
| 9,179,991 B2 | 11/2015 | Gozzi et al. |
| 9,204,922 B2 | 12/2015 | Hooven |
| 9,211,155 B2 | 12/2015 | Fruland et al. |
| 9,220,874 B2 | 12/2015 | Pillai et al. |
| 9,272,140 B2 | 3/2016 | Gerber |
| 9,277,914 B2 | 3/2016 | Wales et al. |
| 9,345,507 B2 | 5/2016 | Hoey et al. |
| 9,345,867 B2 | 5/2016 | Browning |
| 9,393,007 B2 | 7/2016 | Darois et al. |
| 9,439,643 B2 | 9/2016 | Darois et al. |
| 9,459,751 B2 | 10/2016 | Weaver et al. |
| 9,526,555 B2 | 12/2016 | Hoey et al. |
| 9,561,025 B2 | 2/2017 | Stone et al. |
| 9,592,044 B2 | 3/2017 | Weir et al. |
| 9,597,145 B2 | 3/2017 | Nelson et al. |
| 9,668,803 B2 | 6/2017 | Bhushan et al. |
| 9,675,373 B2 | 6/2017 | Todd |
| 9,750,492 B2 | 9/2017 | Ziniti et al. |
| 2001/0041916 A1 | 11/2001 | Bonutti |
| 2001/0044639 A1 | 11/2001 | Levinson |
| 2002/0049453 A1 | 4/2002 | Nobles et al. |
| 2002/0095064 A1 | 7/2002 | Beyar |
| 2002/0095154 A1 | 7/2002 | Atkinson |
| 2002/0107540 A1 | 8/2002 | Whalen |
| 2002/0128684 A1 | 9/2002 | Foerster |
| 2002/0161382 A1 | 10/2002 | Neisz |
| 2002/0177866 A1 | 11/2002 | Weikel et al. |
| 2002/0183740 A1 | 12/2002 | Edwards et al. |
| 2002/0193809 A1 | 12/2002 | Meade |
| 2003/0023248 A1 | 1/2003 | Parodi |
| 2003/0040803 A1 | 2/2003 | Rioux et al. |
| 2003/0060819 A1 | 3/2003 | McGovern et al. |
| 2003/0078601 A1 | 4/2003 | Shikhman et al. |
| 2003/0109769 A1 | 6/2003 | Lowery |
| 2003/0120309 A1 | 6/2003 | Colleran et al. |
| 2003/0130575 A1 | 7/2003 | Desai |
| 2003/0144570 A1 | 7/2003 | Hunter et al. |
| 2003/0176883 A1 | 9/2003 | Sauer et al. |
| 2003/0191497 A1 | 10/2003 | Cope |
| 2003/0199860 A1 | 10/2003 | Loeb |
| 2003/0204195 A1 | 10/2003 | Keane |
| 2003/0236535 A1 | 12/2003 | Onuki |
| 2004/0010301 A1 | 1/2004 | Kindlein et al. |
| 2004/0030217 A1 | 2/2004 | Yeung |
| 2004/0043052 A1 | 3/2004 | Hunter |
| 2004/0078046 A1 | 4/2004 | Barzell |
| 2004/0122456 A1 | 6/2004 | Saadat |
| 2004/0122474 A1 | 6/2004 | Gellman |
| 2004/0143343 A1 | 7/2004 | Grocela |
| 2004/0147958 A1 | 7/2004 | Lam |
| 2004/0162568 A1 | 8/2004 | Saadat et al. |
| 2004/0167635 A1 | 8/2004 | Yachia et al. |
| 2004/0172046 A1 | 9/2004 | Hlavka et al. |
| 2004/0193191 A1 | 9/2004 | Starksen |
| 2004/0193194 A1 | 9/2004 | Laufer |
| 2004/0194790 A1 | 10/2004 | Laufer |
| 2004/0215181 A1 | 10/2004 | Christopherson et al. |
| 2004/0230316 A1 | 11/2004 | Cioanta et al. |
| 2004/0243178 A1 | 12/2004 | Haut |
| 2004/0243179 A1 | 12/2004 | Foerster |
| 2004/0243180 A1 | 12/2004 | Donnelly |
| 2004/0243227 A1 | 12/2004 | Starksen |
| 2004/0260345 A1 | 12/2004 | Foerster |
| 2005/0010203 A1 | 1/2005 | Edwards |
| 2005/0033403 A1 | 2/2005 | Ward et al. |
| 2005/0055087 A1 | 3/2005 | Starksen |
| 2005/0059929 A1 | 3/2005 | Bolmsjo et al. |
| 2005/0065550 A1 | 3/2005 | Starksen |
| 2005/0101982 A1 | 5/2005 | Ravenscroft et al. |
| 2005/0107811 A1 | 5/2005 | Starksen |
| 2005/0107812 A1 | 5/2005 | Starksen |
| 2005/0137716 A1 | 6/2005 | Gross |
| 2005/0154401 A1 | 7/2005 | Weldon |
| 2005/0165272 A1 | 7/2005 | Okada |
| 2005/0171522 A1 | 8/2005 | Christopherson |
| 2005/0177181 A1 | 8/2005 | Kagan |
| 2005/0203344 A1 | 9/2005 | Orban |
| 2005/0203550 A1 | 9/2005 | Laufer |
| 2005/0216040 A1 | 9/2005 | Gertner |
| 2005/0216078 A1 | 9/2005 | Starksen |
| 2005/0222557 A1 | 10/2005 | Baxter et al. |
| 2005/0251157 A1 | 11/2005 | Saadat |
| 2005/0251159 A1 | 11/2005 | Ewers et al. |
| 2005/0251177 A1 | 11/2005 | Saadat |
| 2005/0251206 A1 | 11/2005 | Maahs et al. |
| 2005/0267405 A1 | 12/2005 | Shah |
| 2005/0273138 A1 | 12/2005 | To |
| 2005/0283189 A1 | 12/2005 | Rosenblatt |
| 2005/0288694 A1 | 12/2005 | Solomon |
| 2006/0004410 A1 | 1/2006 | Nobis et al. |
| 2006/0020276 A1 | 1/2006 | Saadat et al. |
| 2006/0025750 A1 | 2/2006 | Starksen |
| 2006/0025784 A1 | 2/2006 | Starksen |
| 2006/0025789 A1 | 2/2006 | Laufer |
| 2006/0025819 A1 | 2/2006 | Nobis |
| 2006/0026750 A1 | 2/2006 | Ballance |
| 2006/0030884 A1 | 2/2006 | Yeung |
| 2006/0058817 A1 | 3/2006 | Starksen |
| 2006/0079880 A1 | 4/2006 | Sage et al. |
| 2006/0079881 A1 | 4/2006 | Christopherson et al. |
| 2006/0089646 A1 | 4/2006 | Bonutti |
| 2006/0095058 A1 | 5/2006 | Sivan et al. |
| 2006/0167477 A1 | 7/2006 | Arcia |
| 2006/0178680 A1 | 8/2006 | Nelson et al. |
| 2006/0199996 A1 | 9/2006 | Caraballo et al. |
| 2006/0241694 A1 | 10/2006 | Cerundolo |
| 2006/0265042 A1* | 11/2006 | Catanese et al. ............ 623/1.11 |
| 2006/0271032 A1 | 11/2006 | Chin et al. |
| 2006/0276481 A1 | 12/2006 | Evrard et al. |

(56) References Cited

U.S. PATENT DOCUMENTS

| | | | |
|---|---|---|---|
| 2006/0276871 A1* | 12/2006 | Lamson et al. | 623/1.11 |
| 2006/0282081 A1 | 12/2006 | Fanton | |
| 2007/0049929 A1 | 3/2007 | Catanese | |
| 2007/0049970 A1 | 3/2007 | Belef | |
| 2007/0060931 A1 | 3/2007 | Hamilton | |
| 2007/0073322 A1 | 3/2007 | Mikkaichi et al. | |
| 2007/0073342 A1 | 3/2007 | Stone et al. | |
| 2007/0088362 A1 | 4/2007 | Bonutti | |
| 2007/0100421 A1 | 5/2007 | Griffin | |
| 2007/0112385 A1 | 5/2007 | Conlon | |
| 2007/0142846 A1 | 6/2007 | Catanese | |
| 2007/0173888 A1 | 7/2007 | Gertner | |
| 2007/0179491 A1 | 8/2007 | Kratoska et al. | |
| 2007/0179496 A1 | 8/2007 | Swoyer et al. | |
| 2007/0198038 A1 | 8/2007 | Cohen et al. | |
| 2007/0260259 A1 | 11/2007 | Fanton | |
| 2008/0009888 A1 | 1/2008 | Ewers | |
| 2008/0021445 A1 | 1/2008 | Elmouelhi | |
| 2008/0021485 A1 | 1/2008 | Catanese et al. | |
| 2008/0033458 A1 | 2/2008 | McLean | |
| 2008/0033488 A1 | 2/2008 | Catanese | |
| 2008/0039833 A1 | 2/2008 | Catanese et al. | |
| 2008/0039872 A1 | 2/2008 | Catanese et al. | |
| 2008/0039874 A1 | 2/2008 | Catanese | |
| 2008/0039875 A1 | 2/2008 | Catanese | |
| 2008/0039893 A1 | 2/2008 | McLean | |
| 2008/0039894 A1 | 2/2008 | Catanese | |
| 2008/0039921 A1 | 2/2008 | Wallsten et al. | |
| 2008/0045978 A1 | 2/2008 | Kuhns | |
| 2008/0051810 A1 | 2/2008 | To et al. | |
| 2008/0058710 A1 | 3/2008 | Wilk | |
| 2008/0065120 A1 | 3/2008 | Zannis | |
| 2008/0082113 A1 | 4/2008 | Bishop | |
| 2008/0086172 A1 | 4/2008 | Martin | |
| 2008/0091220 A1 | 4/2008 | Chu | |
| 2008/0091237 A1 | 4/2008 | Schwartz | |
| 2008/0119874 A1 | 5/2008 | Merves | |
| 2008/0154378 A1 | 6/2008 | Pelo | |
| 2008/0161852 A1 | 7/2008 | Kaiser et al. | |
| 2008/0195145 A1 | 8/2008 | Bonutti | |
| 2008/0208220 A1 | 8/2008 | Shiono | |
| 2008/0228202 A1 | 9/2008 | Cropper | |
| 2008/0269737 A1 | 10/2008 | Elmouelhi | |
| 2009/0012537 A1 | 1/2009 | Green | |
| 2009/0018553 A1 | 1/2009 | McLean et al. | |
| 2009/0060977 A1 | 3/2009 | Lamson et al. | |
| 2009/0112234 A1 | 4/2009 | Crainich et al. | |
| 2009/0112537 A1 | 4/2009 | Okumura | |
| 2009/0118762 A1 | 5/2009 | Crainch et al. | |
| 2009/0177288 A1 | 7/2009 | Wallsten | |
| 2009/0198227 A1 | 8/2009 | Prakash | |
| 2010/0010631 A1 | 1/2010 | Otte et al. | |
| 2010/0023022 A1 | 1/2010 | Zeiner et al. | |
| 2010/0023024 A1 | 1/2010 | Zeiner et al. | |
| 2010/0023025 A1 | 1/2010 | Zeiner et al. | |
| 2010/0023026 A1 | 1/2010 | Zeiner et al. | |
| 2010/0030262 A1 | 2/2010 | McLean | |
| 2010/0030263 A1 | 2/2010 | Cheng et al. | |
| 2010/0049188 A1 | 2/2010 | Nelson et al. | |
| 2010/0063542 A1 | 3/2010 | van der Burg | |
| 2010/0114162 A1 | 5/2010 | Bojarski et al. | |
| 2010/0130815 A1 | 5/2010 | Gross et al. | |
| 2010/0286106 A1 | 11/2010 | Gat | |
| 2010/0286679 A1 | 11/2010 | Hoey | |
| 2010/0298948 A1 | 11/2010 | Hoey et al. | |
| 2010/0324669 A1 | 12/2010 | Hlavka et al. | |
| 2011/0040312 A1* | 2/2011 | Lamson et al. | 606/151 |
| 2011/0046648 A1 | 2/2011 | Johnston | |
| 2011/0060349 A1 | 3/2011 | Cheng et al. | |
| 2011/0077676 A1 | 3/2011 | Sivan et al. | |
| 2011/0144423 A1* | 6/2011 | Tong | A61F 2/04 600/37 |
| 2011/0152839 A1 | 6/2011 | Cima et al. | |
| 2011/0160747 A1 | 6/2011 | McLean | |
| 2011/0166564 A1 | 7/2011 | Merrick | |
| 2011/0190758 A1 | 8/2011 | Lamson et al. | |
| 2011/0196393 A1 | 8/2011 | Eliachar et al. | |
| 2011/0202052 A1 | 8/2011 | Gelbart et al. | |
| 2011/0218387 A1 | 9/2011 | Lamson et al. | |
| 2011/0245828 A1 | 10/2011 | Baxter et al. | |
| 2011/0276081 A1 | 11/2011 | Kilemnik | |
| 2011/0276086 A1 | 11/2011 | Al-Qbandi et al. | |
| 2012/0010645 A1 | 1/2012 | Feld | |
| 2012/0059387 A1 | 3/2012 | Schanz et al. | |
| 2012/0165837 A1 | 6/2012 | Belman et al. | |
| 2012/0203250 A1 | 8/2012 | Weir et al. | |
| 2012/0245600 A1 | 9/2012 | McLean et al. | |
| 2012/0265006 A1 | 10/2012 | Makower et al. | |
| 2013/0096582 A1 | 4/2013 | Cheng | |
| 2013/0178871 A1 | 7/2013 | Koogle et al. | |
| 2013/0211431 A1 | 8/2013 | Wei | |
| 2013/0253574 A1 | 9/2013 | Catanese et al. | |
| 2013/0253662 A1 | 9/2013 | Lamson et al. | |
| 2013/0261383 A1 | 10/2013 | Catanese et al. | |
| 2013/0261665 A1 | 10/2013 | Yeung et al. | |
| 2013/0267772 A1 | 10/2013 | Catanese | |
| 2013/0268001 A1 | 10/2013 | Catanese et al. | |
| 2013/0274799 A1 | 10/2013 | Catanese | |
| 2013/0289342 A1 | 10/2013 | Tong | |
| 2013/0296889 A1 | 11/2013 | Tong | |
| 2013/0296935 A1 | 11/2013 | McLean | |
| 2013/0325143 A1 | 12/2013 | Lamson et al. | |
| 2014/0005473 A1 | 1/2014 | Catanese et al. | |
| 2014/0005690 A1 | 1/2014 | Catanese et al. | |
| 2014/0012192 A1 | 1/2014 | Bar-On et al. | |
| 2014/0088587 A1 | 3/2014 | Merrick et al. | |
| 2014/0221981 A1 | 8/2014 | Cima et al. | |
| 2014/0236230 A1 | 8/2014 | Johnston et al. | |
| 2014/0288637 A1 | 9/2014 | Clerc et al. | |
| 2015/0112299 A1 | 4/2015 | Forbes et al. | |
| 2015/0157309 A1 | 6/2015 | Bird | |
| 2015/0257908 A1 | 9/2015 | Chao et al. | |
| 2015/0335393 A1 | 11/2015 | Ciulla et al. | |
| 2016/0000455 A1 | 1/2016 | Golan et al. | |
| 2016/0038087 A1 | 2/2016 | Hunter | |
| 2016/0051735 A1 | 2/2016 | Slepian | |
| 2016/0081736 A1 | 3/2016 | Hoey et al. | |
| 2016/0089140 A1 | 3/2016 | Kawaura et al. | |
| 2016/0096009 A1 | 4/2016 | Feld | |
| 2016/0120647 A1 | 5/2016 | Rogers et al. | |
| 2016/0206370 A1 | 7/2016 | Fruland et al. | |
| 2016/0242894 A1 | 8/2016 | Davis | |
| 2016/0302904 A1 | 10/2016 | Ogdahl et al. | |
| 2016/0317180 A1 | 11/2016 | Kilemnik | |
| 2017/0000598 A1 | 1/2017 | Bachar | |
| 2017/0128741 A1 | 5/2017 | Keltner et al. | |
| 2017/0135830 A1 | 5/2017 | Harkin et al. | |

FOREIGN PATENT DOCUMENTS

| | | |
|---|---|---|
| CN | 101795641 A | 8/2010 |
| CN | 102112064 B | 6/2014 |
| CN | 105919695 A | 9/2016 |
| DE | 10159470 A1 | 6/2003 |
| EP | 0246836 | 12/1991 |
| EP | 0274846 B1 | 2/1994 |
| EP | 0632999 A1 | 1/1995 |
| EP | 0464480 | 3/1995 |
| EP | 0667126 A1 | 8/1995 |
| EP | 1482841 A1 | 12/2004 |
| EP | 1082941 | 3/2005 |
| EP | 1016377 | 4/2006 |
| EP | 1006909 | 1/2007 |
| EP | 1852071 A2 | 11/2007 |
| EP | 1584295 | 2/2008 |
| EP | 1670361 | 4/2008 |
| EP | 1331886 | 12/2008 |
| EP | 1482840 B1 | 12/2008 |
| EP | 1884198 | 3/2010 |
| EP | 2243507 A1 | 10/2010 |
| EP | 1884199 | 1/2011 |
| EP | 1484023 | 5/2011 |
| EP | 2345373 A1 | 7/2011 |
| EP | 2345374 A1 | 7/2011 |

(56) References Cited

FOREIGN PATENT DOCUMENTS

| | | |
|---|---|---|
| EP | 2049023 B1 | 12/2014 |
| EP | 3167845 A1 | 5/2017 |
| FR | 2750031 A1 | 12/1997 |
| JP | 5836559 A | 3/1983 |
| JP | 09122134 A | 5/1997 |
| JP | H09122134 A | 5/1997 |
| JP | 3370300 B2 | 1/2003 |
| JP | 2004344427 A | 12/2004 |
| JP | 2009521278 A | 6/2009 |
| JP | 2011529745 A | 12/2011 |
| JP | 2012143622 A | 8/2012 |
| KR | 20060009698 A | 2/2006 |
| RU | 2062121 C1 | 10/1989 |
| RU | 2112571 C1 | 6/1998 |
| RU | 2128012 C1 | 3/1999 |
| RU | 2221501 C2 | 1/2004 |
| WO | WO-87001270 | 3/1987 |
| WO | WO-92010142 | 6/1992 |
| WO | WO-93004727 | 3/1993 |
| WO | WO-93015664 | 8/1993 |
| WO | 1995000818 A1 | 1/1995 |
| WO | 2000040119 A1 | 7/2000 |
| WO | WO-2001026588 | 4/2001 |
| WO | 2001039671 A1 | 6/2001 |
| WO | 2001049195 A1 | 7/2001 |
| WO | WO-01095818 | 12/2001 |
| WO | 2002032321 A1 | 4/2002 |
| WO | WO-02030335 | 4/2002 |
| WO | 2002058577 A1 | 8/2002 |
| WO | WO-2001028432 | 8/2002 |
| WO | WO-03039334 | 5/2003 |
| WO | WO-03077772 | 9/2003 |
| WO | WO-02028289 | 11/2003 |
| WO | 2004000159 A2 | 12/2003 |
| WO | WO-2004017845 | 3/2004 |
| WO | WO-2004019787 | 3/2004 |
| WO | WO-2004019788 | 3/2004 |
| WO | WO-2004030569 | 4/2004 |
| WO | 2004066875 A1 | 8/2004 |
| WO | 2004080529 A2 | 9/2004 |
| WO | WO-2004103189 | 12/2004 |
| WO | WO-2005034738 | 4/2005 |
| WO | WO-2005065412 | 7/2005 |
| WO | WO-2005094447 | 10/2005 |
| WO | 2006127241 A2 | 11/2006 |
| WO | 2006127431 A2 | 11/2006 |
| WO | 2007048437 A1 | 5/2007 |
| WO | WO-2007053516 | 5/2007 |
| WO | WO-2007064906 | 6/2007 |
| WO | 2007075981 A2 | 7/2007 |
| WO | 2008002340 A2 | 1/2008 |
| WO | WO-2008006084 | 1/2008 |
| WO | WO-2008014191 | 1/2008 |
| WO | WO-2008043044 | 4/2008 |
| WO | WO-2008043917 | 4/2008 |
| WO | 2008097942 A1 | 8/2008 |
| WO | 2008132735 A1 | 11/2008 |
| WO | 2008142677 A2 | 11/2008 |
| WO | WO-2009009617 | 1/2009 |
| WO | 2009072131 A2 | 6/2009 |
| WO | WO-2010011832 | 1/2010 |
| WO | 2010014821 A2 | 2/2010 |
| WO | 2010014825 A1 | 2/2010 |
| WO | 2010065214 A2 | 6/2010 |
| WO | 2010086849 A1 | 8/2010 |
| WO | 2010106543 A2 | 9/2010 |
| WO | 2011084712 A1 | 7/2011 |
| WO | 2012018446 A2 | 2/2012 |
| WO | 2012079548 A1 | 6/2012 |
| WO | 2012079549 A2 | 6/2012 |
| WO | 2012091952 A2 | 7/2012 |
| WO | 2012091955 A2 | 7/2012 |
| WO | 2012091956 A2 | 7/2012 |
| WO | WO-2012091954 | 7/2012 |
| WO | 2012123950 A2 | 9/2012 |
| WO | 2014003987 A1 | 1/2014 |
| WO | 2014035506 A2 | 3/2014 |
| WO | 2014145381 A1 | 9/2014 |
| WO | 2014153219 A1 | 9/2014 |
| WO | 2014200764 A1 | 12/2014 |
| WO | 2015101975 A1 | 7/2015 |
| WO | 2016134166 A1 | 8/2016 |
| WO | 2017017499 A1 | 2/2017 |
| WO | 2017081326 A2 | 5/2017 |
| WO | 2017112856 A1 | 6/2017 |

OTHER PUBLICATIONS

Borzhievski, "Tactics of the Surgical Treatment of Patients With Prostatic Adenoma and Acute Urinary Retention", Urologia Nefrol (Mosk), (1), (1987), 39-43.
"European Application Serial No. 06845991.6, Extended European Search Report dated Mar. 22, 2013", 7 pgs.
"European Application Serial No. 07840462.1, Extended European Search Report dated May 29, 2012", 8 pgs.
"European Application Serial No. 08729001.1, Extended European Search Report dated Feb. 4, 2014", 6 pgs.
"European Application Serial No. 08729001.1, Supplementary European Search Report dated Feb. 21, 2014", 1 pg.
"European Application Serial No. 11154962.1, European Search Report dated May 19, 2011", 2 pgs.
"European Application Serial No. 11154976, European Search Report dated May 19, 2011", 2 pgs.
Hartung, Rudolf, "Instrumentelle Therapie der benegnen Prostatahyperplasie", Medizin, Deutsches Arzteblatt 97, Heft 15, (Apr. 2000), 8 pgs.
Hofner, Klaus, "Operative Therapie des benignen Prostatasyndroms", Medizin, Dtsch Arztebl, 194(36), (2007), 6 pgs.
Hubmann, R, "Geschichte der transurethralen Prostataeingriffe", Geschichte der Medizin, Urologe (B), 40, (2000), 152-160.
"International Application Serial No. PCT/US06/19372, International Search Report dated May 2, 2008", 1pg.
"International Application Serial No. PCT/US06/48962, International Search Report dated Dec. 10, 2008", 2 pgs.
"International Application Serial No. PCT/US2007/74019, International Search Report dated Jul. 25, 2008", 1 pg.
"International Application Serial No. PCT/US2008/053001, International Search Report dated Jun. 17, 2008", 3 pg.
"International Application Serial No. PCT/US2008/069560, International Search Report dated Sep. 8, 2008", 1 pg.
"International Application Serial No. PCT/US2009/052271, International Search Report dated Apr. 7, 2010", 6 pgs.
"International Application Serial No. PCT/US2009/052275, International Search Report dated Oct. 9, 2009", 4 pgs.
"International Application Serial No. PCT/US2011/041200, International Search Report dated Feb. 17, 2012", 5 pgs.
"International Application Serial No. PCT/US2011/065348, International Search Report dated Jun. 21, 2012", 5 pgs.
"International Application Serial No. PCT/US2011/065358, International Search Report dated Jun. 21, 2012", 9 pgs.
"International Application Serial No. PCT/US2011/065377, International Search Report dated Aug. 29, 2012", 11 pgs.
"International Application Serial No. PCT/US2011065386, International Search Report dated Jun. 28, 2012", 4 pgs.
"Japanese Application Serial No. 2012-104915, Office Action dated Mar. 17, 2014", 2 pgs.
Jonas, U, "Benigne Prostatahyperplasie", Der Urologe, 45, (2006), 134-144.
Reich, O, "Benignes Prostatasyndrom (BPS)", Der Urologe, A Issue, vol. 45, No. 6, (Jun. 2006), 769-782.
Schauer, P, "New applications for endoscopy: the emerging field of endoluminal and transgastric bariatric surgery", Surgical Endoscopy, (Apr. 24, 2006), 10 pgs.
Sharp, Howard T, "Instruments and Methods—The 4-S Modification of the Roeder Knot: How to Tie It", Obstetrics & Gynecology, vol. 90, No. 6, (Dec. 1, 1997), 1004-1006.
Trapeznikov, "New Technologies in the Treatment of Benign Prostatic Hyperplasia", Urologia Nefrol(Mosk), (4), (Jul.-Aug. 1996), 41-47.

(56) References Cited

OTHER PUBLICATIONS

Yeung, Jeff, "Treating Urinary Stress Incontinence Without Incision with Endoscopic Suture Anchor & Approximating Device", Aleeva Medical, Inc, (2007), 31 pgs.
Bacharova, O.A., et al. "The Effect of Rhodiolae rosea Extract on Incidence Rate of Superficial Bladder Carcinoma Relapses", Kozin 1995.
European Search Report for EP Application No. 06770621.8, dated Sep. 20, 2012.
European Search Report for EP Application No. 08772483.7, dated Feb. 12, 2015.
European Search Report for EP Application No. 11154962.2, dated May 19, 2011.
European Search Report for EP Application No. 11814950.9, dated Sep. 8, 2015.
European Search Report for EP Application No. 11852778.7, dated Nov. 19, 2015.
European Search Report for EP Application No. 11854148.1, dated Oct. 20, 2017.
European Search Report for EP Application No. 13810314.8, dated Apr. 6, 2016.
European Search Report for EP Application No. 17150545.6, dated Sep. 11, 2017.
International Search Report for PCT Application No. PCT/US2013/044035, dated Sep. 6, 2013.
Kruck, S., et al., "Aktuelle Therapiemoglichkeiten des Benignen Prostata-Syndroms", J Urol Urogynakol, 2009; 16 (1): 19-22.

\* cited by examiner

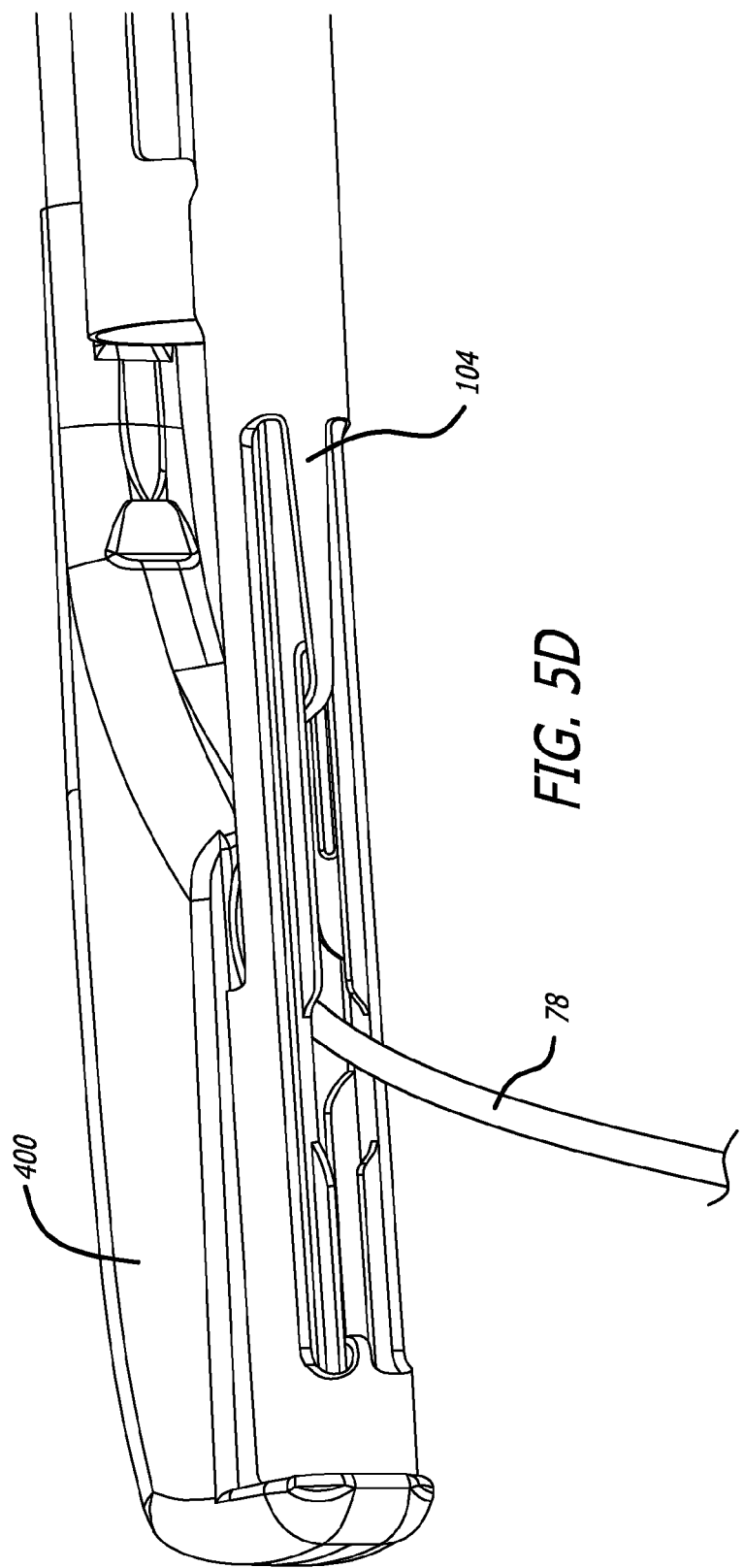

SYSTEM FOR DELIVERING ANCHORS FOR TREATING INCONTINENCE

FIELD OF THE INVENTION

The present invention relates generally to medical devices and methods, and more particularly to systems and associated methods for manipulating or retracting tissues and anatomical or other structures within the body of human or animal subjects for the purpose of treating incontinence.

Urinary incontinence is any involuntary leakage of urine. It almost always results from an underlying treatable medical condition.

Normal continence involves a balance between urethral closure and detrusor muscle activity. The body stores urine in the urinary bladder. The bladder connects to the urethra, the tube through which urine leaves the body. Urethral pressure normally exceeds bladder pressure, resulting in urine remaining in the bladder. When sphincter muscles surrounding the urethra relax, urine is passed out of the body. Incontinence will occur if the bladder muscles suddenly contract or muscles surrounding the urethra suddenly relax.

There are a number of causes of incontinence. An enlarged prostate may be cause of incontinence, particularly urge incontinence, in men after the age of 40. Sometimes prostate cancer may also be associated with urinary incontinence. While urinary incontinence affects older men more often than younger men, the onset of incontinence can happen at any age. Recent estimates by the National Institutes of Health (NIH) suggest that 17 percent of men over age 60, an estimated 600,000 men, experience urinary incontinence, with this percentage increasing with age. Incontinence is treatable and often curable at all ages. Incontinence in men usually occurs because of problems with muscles that help to hold or release urine.

Incontinence in women can result from physical changes from pregnancy and childbirth. Menopause can also contribute to stress incontinence. Incontinence can worsen during the week before the menstrual period. At that time, lowered estrogen levels may lead to lower muscular pressure around the urethra, increasing chances of leakage. The incidence of incontinence increases following menopause, similarly because of lowered estrogen levels. As much as 35% of the total population over the age of 60 years is estimated to be incontinent, with women twice as likely as men to experience incontinence. One in three women over the age of 60 years are estimated to have bladder control problems. Incontinence is expensive to the health care system and nursing home industry as more than 50% of nursing facility admissions are related to incontinence. Further, disorders like multiple sclerosis, spina bifida, Parkinson's disease, strokes and spinal cord injury can all interfere with nerve function of the bladder.

There are also a number of different types of incontinence. Stress incontinence, also known as effort incontinence, is due essentially to insufficient strength of the pelvic floor muscles. Urge incontinence is generally due to involuntary loss of urine occurring for no apparent reason while suddenly feeling the need or urge to urinate. Overflow incontinence refers to people finding that they cannot stop their bladders from constantly dribbling or continuing to dribble for some time after they have passed urine.

Incontinence treatment options include behavior management, medications and surgery. Some approaches address the problem symptomatically, and can be applicable to more than one type of incontinence. Absorbent pads and various types of urinary catheters may be employed to help certain individuals. Men also can use an external urine collection device that is worn around the penis. These are traditionally referred to as condom catheters. Absorbent products include shields, undergarments, protective underwear, briefs, diapers, adult diapers and underpads.

Benign Prostatic Hyperplasia (BPH) is one of the most common medical conditions that affect men, especially elderly men. It has been reported that, in the United States, more than half of all men have histopathologic evidence of BPH by age 60 and, by age 85, approximately 9 out of 10 men suffer from the condition. Moreover, the incidence and prevalence of BPH are expected to increase as the average age of the population in developed countries increases. Although BPH is rarely life threatening, it can lead to numerous clinical conditions including urinary retention, renal insufficiency, recurrent urinary tract infection, incontinence, hematuria, and bladder stones.

The prostate gland enlarges throughout a man's life. In some men, the prostatic capsule around the prostate gland may prevent the prostate gland from enlarging further. This causes the inner region of the prostate gland to squeeze the urethra. This pressure on the urethra increases resistance to urine flow through the region of the urethra enclosed by the prostate. Thus the urinary bladder has to exert more pressure to force urine through the increased resistance of the urethra. Chronic over-exertion causes the muscular walls of the urinary bladder to remodel and become stiffer. This combination of increased urethral resistance to urine flow and stiffness and hypertrophy of urinary bladder walls leads to a variety of lower urinary tract symptoms (LUTS) that may severely reduce the patient's quality of life. These symptoms include weak or intermittent urine flow while urinating, straining when urinating, hesitation before urine flow starts, feeling that the bladder has not emptied completely even after urination, dribbling at the end of urination or leakage afterward, increased frequency of urination particularly at night, urgent need to urinate etc.

In addition to patients with BPH, LUTS may also be present in patients with prostate cancer, prostate infections, and chronic use of certain medications (e.g. ephedrine, pseudoephedrine, phenylpropanolamine, antihistamines such as diphenhydramine, chlorpheniramine etc.) that cause urinary retention especially in men with prostate enlargement.

Surgical procedures for treating BPH symptoms include Transurethal Resection of Prostate (TURP), Transurethral Electrovaporization of Prostate (TVP), Transurethral Incision of the Prostate (TUIP), Laser Prostatectomy and Open Prostatectomy. Minimally invasive procedures for treating BPH symptoms include Transurethral Microwave Thermotherapy (TUMT), Transurethral Needle Ablation (TUNA), Interstitial Laser Coagulation (ILC), and Prostatic Stents.

There have been advances in developing minimally invasive devices and methods for lifting, stabilizing and repositioning of tissues. There remains, however, a need for the development of new devices and methods that can be used for various procedures where it is desired to lift, compress, support, stabilize, modify or reposition tissues to treat incontinence. In particular, there is a need for alternative apparatus and treatment approaches for the purpose of manipulating the urethra and tissues surrounding the urethra. Various structures ensuring an effective interventional procedure have been found to be needed.

The present disclosure addresses these and other needs.

SUMMARY

Briefly and in general terms, the present invention is directed towards an apparatus and method for deploying an anchor assembly within a patient's body to accomplish treating incontinence. A delivery device is provided to access the anatomy targeted for the interventional procedure, such as a urethra. The delivery device facilitates the implantation of the anchor assembly in a manner accomplishing retraction or displacement of tissue. The delivery device is configured to accomplish the assembly of the anchor assembly in situ and can also automatically determine a length of the anchor assembly.

In one approach, one or more anchor assemblies are configured to reposition, stabilize or reduce the mobility of a portion of a urethra upwardly with respect to surrounding tissue. The anchor also can be configured to reduce a lumen size of the urethra. A proximal portion of the anchor assembly can be placed within anterior or lateral sections of the urethra. The anchor assemblies can also be positioned laterally relative to the urethra and implanted to maintain a constant position of the urethra against increases in intra-abdominal pressure. Moreover, one or more anchor assemblies can be configured about the prostate to lift or maintain a position of a portion of a urethra in a male patient. In a female patient, a portion of an anchor assembly can be passed through anterior periurethral fascia to the exclusion of or including the urethral lumen, and anchored to surrounding tissue to thereby reposition, stabilize or maintain positioning of a urethra, or reduce or modify the size of the urethra.

The delivery apparatus of the present disclosure includes various subassemblies, which are mobilized via an actuator or other manually accessible structure. The apparatus is sized and shaped so that it can be placed transurethrally or it can be configured to be inserted through a surgical incision so that access to tissue surrounding a urethra can be accessed. The operation of the subassemblies is coordinated and synchronized to ensure accurate and precise implantation of an anchor assembly. In one embodiment, the delivery device is embodied in a tissue retraction assembly.

In one particular aspect, the present invention is directed towards a delivery device, which accomplishes the delivery of a first or distal anchor assembly component at a first location within a patient's body and the delivery of a second or proximal anchor assembly component at a second location within the patient. The device also accomplishes imparting tension during delivery to a connector to hold it while attaching the proximal anchor in situ. The procedure can be viewed employing a scope inserted in the device. Also, the delivery device can be sized and shaped to be compatible inside a sheath up to 24F, preferably a 19F sheath or smaller.

The anchor assembly can be configured to accomplish approximating, retracting, lifting, compressing, supporting, stabilizing, or repositioning tissue within the body of a human or animal subject. Moreover, the apparatus configured to deploy the anchor assembly as well as the anchor assembly itself are configured to complement and cooperate with body anatomy. Further, the anchor assembly can be coated or imbedded with therapeutic or diagnostic substances, in particular Botulinum toxin, or a silver ion coating or such substances can be introduced into or near an interventional site by the anchor deployment device or other structure.

In various approaches, the anchor can include a distal anchor connected to a proximal anchor by a connector. The distal anchor has a body with a tail. The proximal anchor can include a pair of spaced members, which are configured to capture and deform the connector there between and prevent the connector from disengaging from the anchor device once engaged. The mechanism of connector attachment and strength of the assembly is a combination of compression of the connector between deformable structure of the anchor as well as disruption of the connector surface by the anchor. The deformable structure provides surface contact and focuses the compressive forces that cause the connector to conform about the anchor.

The anchor assembly can also be characterized by a connector embodying multiple strands. Such strands can be spaced upon delivery of the anchor assembly to provide a larger supporting structure. The anchor assembly can further define a sling structure including a woven connector connecting spaced anchor members.

Various alternative methods of use are contemplated. Thus, a transurethral approach to anchor assembly delivery as well as an approach through a surgical incision are contemplated. The disclosed apparatus can be used to alter flow of a body fluid through a body lumen, such as for the purpose of treating urinary incontinence. Also, the disclosure has a myriad of other potential surgical, therapeutic, cosmetic or reconstructive applications, such as where a tissue, organ, graft or other material requires stabilizing, retracting, lifting, repositioning, compression, modifying or support.

In a specific application, the disclosed apparatus are contemplated to be employed to reposition, stabilize or maintain positioning of a portion of a urethra or can be used to alter or reduce the size of the urethra. In one aspect, an anchoring device housed within a delivery device is inserted into a urethra transurethrally and the delivery device is employed to reconfigure the urethra.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIGS. 5A-D are side and perspective views, depicting one embodiment of a delivery device and various features thereof;

FIG. 5A is a view of a first embodiment of a delivery device;

FIG. 5B is a view of a second embodiment of a delivery device;

FIG. 5C is a view of a third embodiment of a delivery device;

FIG. 5D is a view of a fourth embodiment of a delivery device;

FIG. 6A is a view of a first treatment approach;

FIG. 6B is a view of a second treatment approach;

FIG. 8A is a view of a first further treatment approach;

FIG. 8B is a view of a second further treatment approach;

FIG. 9A is a view of a first further treatment approach;

FIG. 9B is a view of a second further treatment approach;

FIG. 13A is a view of a first further treatment approach;

FIG. 13B is a view of a second further treatment approach;

FIG. 14A is a view of a first alternative approach; and

FIG. 14B is a view of a second alternative approach.

DETAILED DESCRIPTION OF THE PREFERRED EMBODIMENTS

Turning now to the figures, which are provided by way of example and not limitation, the present disclosure is directed to a device configured to deliver an anchor assembly within a patient's body for treatment purposes. The disclosed apparatus can be employed for various medical purposes including but not limited to treating incontinence.

In an aspect of the present invention, one portion of an anchor assembly or implant is positioned and implanted against a first section of anatomy. A second portion of the anchor assembly or implant is then positioned and implanted adjacent to a second section of anatomy for the purpose of retracting, lifting, compressing, stabilizing, supporting or repositioning the second section of anatomy with respect to the first section of anatomy as well as for the purpose of retracting, lifting, compressing, stabilizing, supporting or repositioning the first section of anatomy with respect to the second section of anatomy. It is also to be recognized that both a first and second portion of the anchor assembly can be configured to accomplish the desired retracting, lifting, compressing, stabilizing, supporting or repositioning of anatomy due to tension supplied during delivery via a connector assembly affixed to the first and second portions of the anchor assembly or implant.

Figure 1:
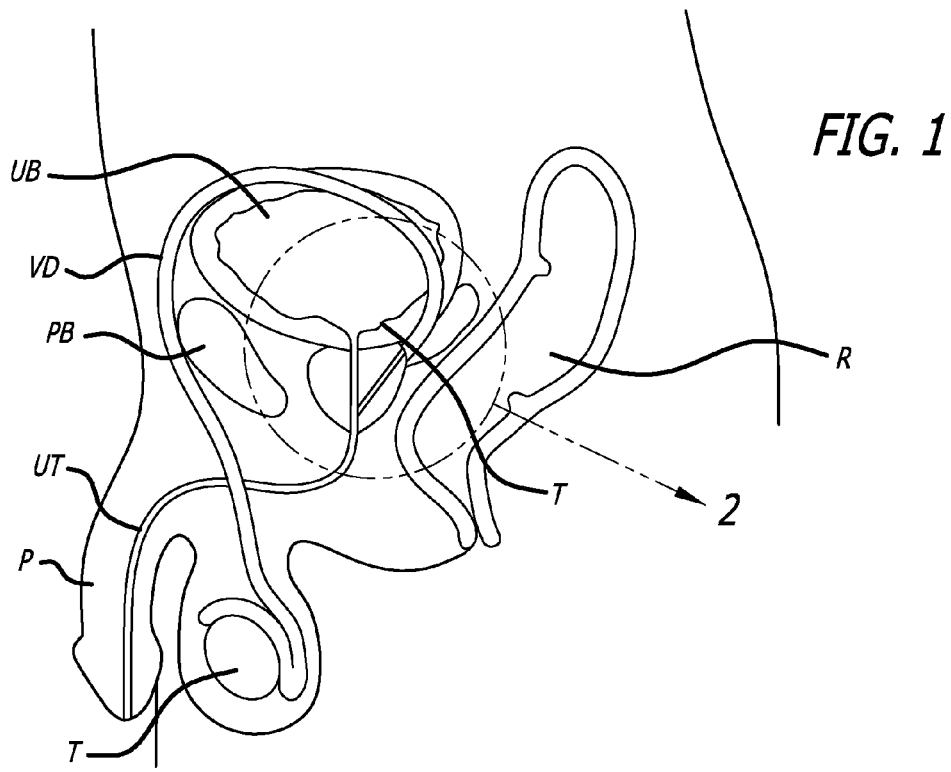
FIG. 1 is a cross-sectional view, depicting anatomy surrounding a urethra in a human male subject.
Figure 2:
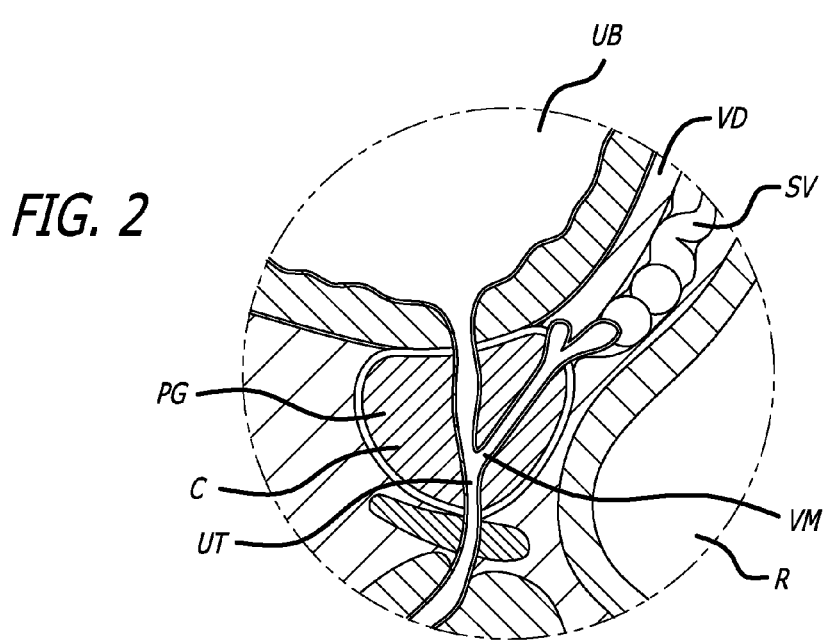
FIG. 2 is an enlarged cross-sectional view, depicting anatomy surrounding a prostate.
Figure 3:
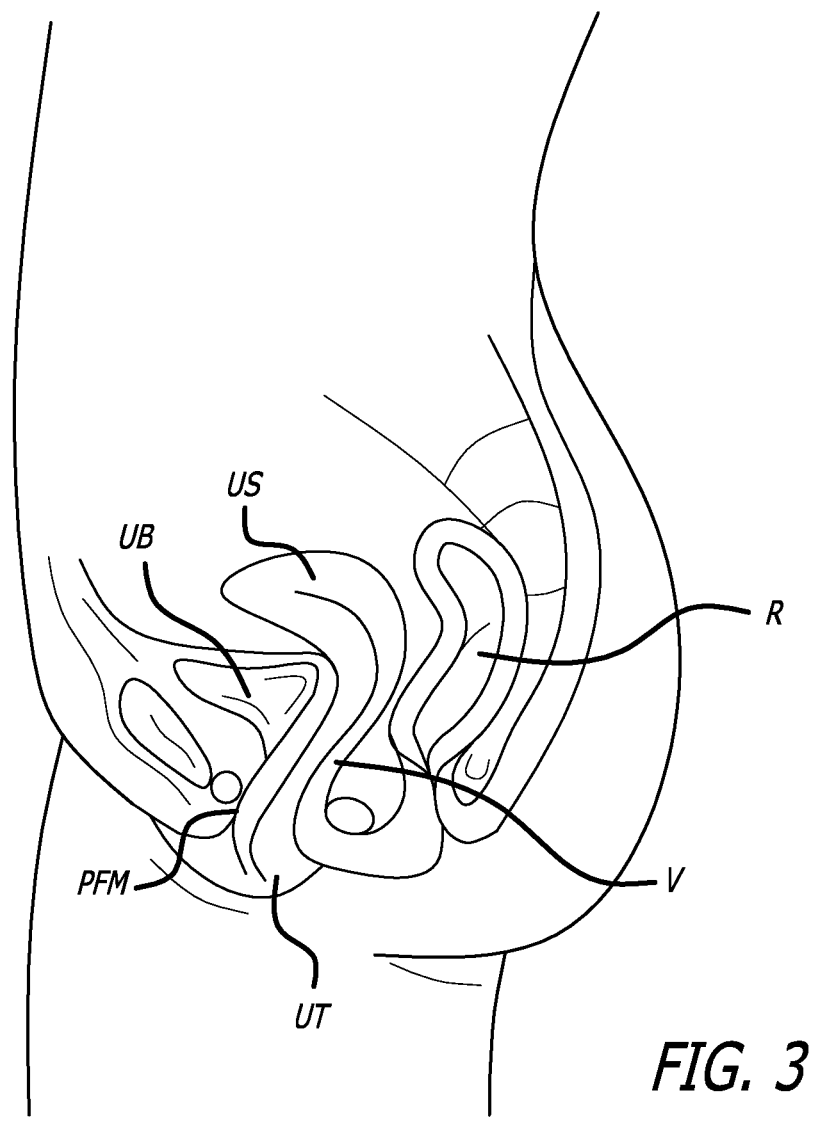
FIG. 3 is a cross-sectional view, depicting anatomy surrounding a urethra in a female subject.

Turning to FIGS. 1-3, various features of urological anatomy of a human subject are presented. With specific reference to FIGS. 1 and 2, in a male subject, the prostate gland PG is a walnut-sized muscular gland found in a male and located adjacent the urinary bladder UB. The urethra UT runs through the prostate gland PG. The prostate gland PG secretes fluid that protects and nourishes sperm. The prostate also contracts during ejaculation of sperm to expel semen and to provide a valve to keep urine out of the semen. A capsule C surrounds the prostate gland PG. The portion of the urethra UT extending through the prostate PG is referred to as the prostatic urethra PU. Distal to the prostatic urethra PU are the membranous urethra MU and bulbous urethra BU portions of the urethra UT. The membranous urethra MU is the most narrow, shortest and least dilatable portion of the urethra. It extends between an apex of the prostate PG to the bulb of the urethra UT.

The urinary bladder UB holds urine. The vasa deferentia VD define ducts through which semen is carried and the seminal vesicles SV secrete seminal fluid. The rectum R is the end segment of the large intestine and through which waste is dispelled. The urethra UT carries both urine and semen out of the body. Thus, the urethra is connected to the urinary bladder UB and provides a passageway to the vasa deferentia VD and seminal vesicles SV.

Further, the trigone T is a smooth triangular region of the bladder. It is sensitive to expansion and signals the brain when the urinary bladder UB is full. The verumontanum VM is a crest in the wall of the urethra UT where the seminal ducts enter. The prostatic urethra is the section of the urethra UT which extends through the prostate.

In a female subject (FIG. 3), the urinary bladder UB also holds urine and extending from the bladder is the urethra UT. The pelvic floor muscle PFM supports the female urinary bladder UB and the position of the urethra UT. The uterus US and vagina V as well as the rectum R are positioned posteriorly of the anatomy defining the urinary system.

Figure 4:
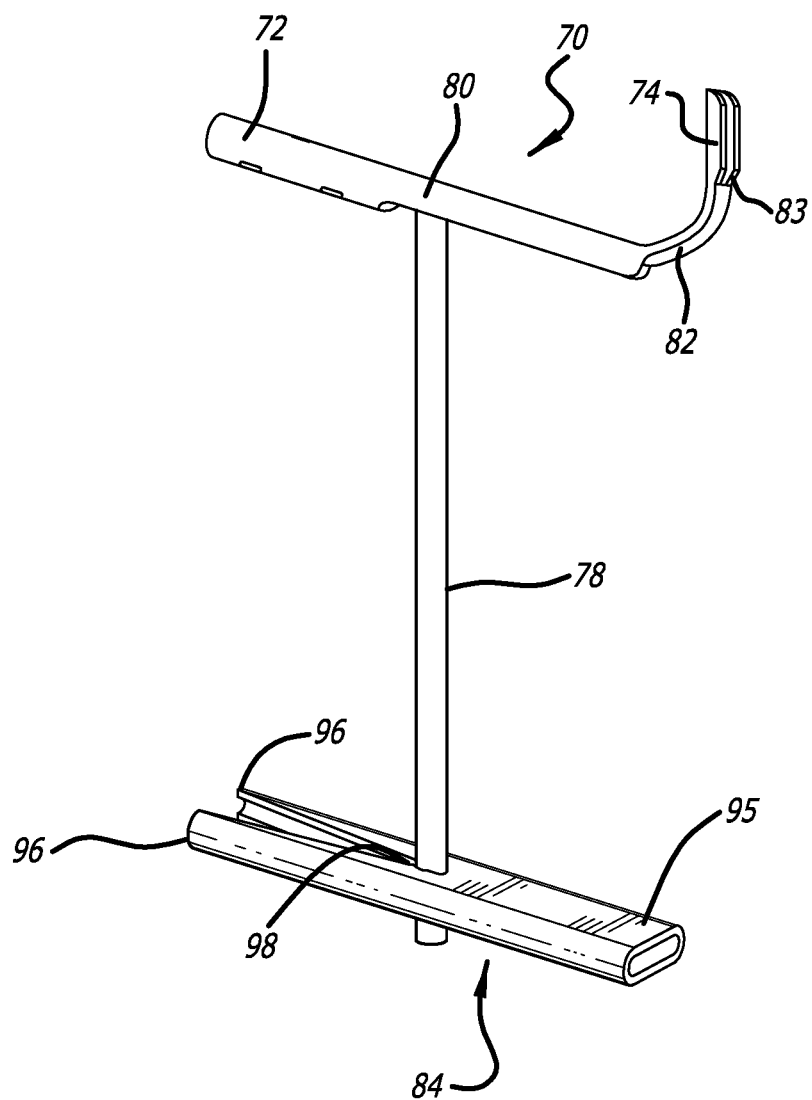
FIG. 4 is a perspective side view, depicting one embodiment of an anchor assembly

In one embodiment (See FIG. 4), the anchor assembly 60 is embodied in a tissue anchor. The tissue anchor is an implant assembly that includes one tubular member, referred to as the capsular anchor or, more generally, distal anchor 70. The distal anchor 70 is preferably connected by a suture (preferably polyester) 78 to a slotted, flattened-tubular member (preferably comprised of stainless steel), referred to as the urethral anchor or proximal anchor 84. In one specific, non-limiting embodiment, the distal anchor 70 is comprised of an electro-polished Nitinol (nickel titanium alloy SE508, 55.8% nickel) tube.

The tissue anchor is designed to be useable in physician's clinical office environment (in contrast to requiring a hospital environment) with a delivery tool. The delivery tool is used through a 19 F sheath in one preferred embodiment, while in another embodiment a sheath size of 21F is employed. In this suture-based, tissue technique, a needle delivery mechanism is used to implant a nitinol distal anchor 70 and attached suture 78. Once the distal anchor 70 and attached suture 78 have been deployed, with the needle retracted and the suture 78 tensioned, the slotted anchor 84 is pushed by the delivery tool and captures the suture 78 transverse to the anchor axis. The flattened portion of the anchor 84 allows the anchor to be held by the tool without rotating so that it will stay oriented properly to ensure the suture enters the space between the prongs. In many of the illustrated embodiments, the seating region in the slotted anchor for the suture is shown in approximately the mid-point of the slotted anchor but it is within the scope of the present invention to locate the seating region closer to one end or the other of the anchor in order to prevent the ends of the prongs of the anchor from digging into tissue after implantation but rather sit more parallel to the tissue, if so desired.

The nitinol tube can be attached to a USP size 0 PET (Poly Ethylene Terephthalate) monofilament suture 78 by thermally forming the suture to locking features on the anchor 70. Referring again to the suture itself, the PET suture is a round monofilament extrusion/pulltrusion composed of a grade 8816 polyethylene terephthalate. Typically, the base material for the suture is annealed at approximately 375 degrees Fahrenheit for approximately 5 minutes in a straight condition. In one non-limiting embodiment, the PET suture 78 has a diameter of 0.015 inches and a tensile strength greater than or equal to 12.7 pounds. It is preferred that the tensile strength be about 6 pounds or greater.

In one embodiment, the proximal anchor 84 is a 316L stainless steel flattened tube that is slotted, electro-polished, and passivated. The anchor is depicted in the figures with a flat surface on the top or bottom but it is within the scope of the present invention that only one of the surfaces be flat and that the surface(s) do not have to be true flat but rather could have a slight dip or protrusion on the flattened surfaces. The slotted anchor 84 includes prongs 96 that grip and deform the suture 78 in the seating region 98 between the spaced prongs 96. It is to be recognized that rather than defining mirrored images, in one or more of the embodiments disclosed herein, the seating region can be formed by staggered structure or one prong can have a longer area defining seating structure than an opposing prong to provide an effective engagement for a particular suture or connector design. The prongs 96 are quite stiff and robust therefore subject to minimal to no deflection. In particular preferred embodiments, the prongs or overall width of the anchor adjacent the seating region 98 expands, after a connector has been seated in the seating region, less than about 0.002 inches (i.e., less than about five percent), more preferably less than about 0.001 inches (i.e., less than about two and half percent). In particular preferred embodiments, the prongs or overall width of the anchor adjacent the ends of the prongs 96 expands, after a connector has been seated in the seating region, less than about 0.0065 inches (i.e., less than about seventeen percent), more preferably less than about 0.006 inches (i.e., less than about fifteen percent). Due to its particular configuration, the slotted anchor 84 also requires less force to deploy onto a suture 78. Being relatively stiff, the prongs 96 of the slotted anchor 84 are significantly more resistant to bending. The four individual edges/faces (two on each prong 96) of the slotted anchor 84 disrupt the surface of the suture 78, both biting into the suture 78 as well as compressing the suture 78 between the slotted prongs 96, including sometimes melting the suture locally due to the pressure and heat created during deployment of the slotted anchor onto the suture. The reduced area of contact provided by this structure as well as multiple planes of engagement of the anchor slot to the connector strengthens connections and prevents inadvertent separation. Additionally, the narrow width between the prongs 96 is substantially smaller than the connector diameter, with the purpose to allow the stiffer prongs to slightly elastically expand over the connector and contribute to anchor retention by means of compression but not intended to receive the connector into this relief slot, which is positioned proximal to the seating portion 98. It is beneficial in some circumstances however for the slotted anchor to be pushed far enough on to the connector such that the connector becomes at least partially seated in the slot inception relief slot so that it becomes pinched and/or wedged. In this circumstance, a two-part compression slot is created wherein the short, narrow part of the slot ensures a good mechanical interlock but may compromise the strength of the suture locally and the second wider part is ensures a good mechanical interlock but without any compromise in the strength of the suture. Notably, the outwardly stepped slot width also has a dimension smaller than the connector diameter, and receives the connector with some interference.

The prongs 96 can be formed from a wide (or flattened) tubular structure. The wider and smoother prongs 96 of the anchor 84 assist in preventing the prongs 96 from irritating and/or damaging tissue, which is more likely to occur with a thinner and pointier leg structure. Further, in one embodiment, the slot in the anchor 84 is configured to create registering and aligning surfaces to the delivery tool (not shown). In several embodiments, the two inner surfaces of the prongs 96 of the slotted anchor 84 are configured as corresponding inwardly facing U-shapes. In this configuration, the inner surfaces of the prongs 96 bite into the suture 78. In still other embodiments, the two inner surfaces of the prongs 96 of the slotted anchor 84 are configured to present a notched geometry. In still other embodiments, the inner surfaces of the prongs are configured with burrs, roughened edges, serrations, etc. to enhance their ability to retain the connector.

Referring now to FIGS. 5A-D, there is shown one embodiment of a delivery device 100. This device is configured to include structure that is capable of both gaining access to an interventional site as well as assembling and implanting one or more anchor assemblies or implants within a patient's body. The delivery device 100 can be configured to assemble and implant a single anchor assembly or implant. The device is further contemplated to be compatible for use with a 19F sheath. The device additionally includes structure configured to receive a conventional remote viewing device (e.g., an endoscope) so that the steps being performed at the interventional site can be observed.

Prior to use of the present device 100, a patient typically undergoes a five day regiment of antibiotics. A local anesthesia can be employed for the interventional procedure. A combination of an oral analgesic with a sedative or hypnotic component can be ingested by the patient. Moreover, topical anesthesia such as lidocaine liquids or gel can be applied to the bladder and urethra.

The anchor delivery device 100 includes a handle assembly 102 connected to an elongate tissue access assembly 104. The elongate tissue access assembly 104 houses components employed to construct an anchor assembly and is sized to fit into a 19F cystoscopic sheath for patient tolerance during a procedure in which the patient is awake rather than under general anesthesia. The tissue access assembly is stiff to allow manual exploration of tissue at an interventional site by leveraging or pushing the handle assembly 102.

The anchor delivery device 100 further includes a number of subassemblies. A handle case assembly 106 including mating handle parts, which form part of the handle assembly 102. The handle assembly 102 is sized and shaped to fit comfortably within an operator's hand and can be formed from conventional materials. Windows can be formed in the handle case assembly 106 to provide access to internal mechanisms of the device so that a manual override is available to the operator in the event the interventional procedure needs to be abandoned.

In one embodiment, the delivery device 100 is equipped with various activatable members, which facilitate assembly and delivery of an anchor assembly at an interventional site. A needle actuator 108 is provided and as described in detail below, effectuates the advancement of a needle assembly (loaded with a first component of an anchor assembly) to an interventional site. In a preferred embodiment, the needle assembly has a needle that moves through a curved trajectory and exits the needle housing in alignment with a handle element, and in particular embodiments, in alignment with the grip. In various other embodiments, the needle housing is oriented such that the needles exits the housing at either the two o'clock or ten o'clock positions relative to a handle grip that is vertical. A needle retraction lever assembly 110 is also provided and when actuated causes the needle assembly to be withdrawn and expose the first anchor component. This action and the structure involved is also described in detail below. Finally, the delivery device 100 is equipped with a rear or proximal anchor actuator assembly 112, which as fully described below, upon actuation, accomplishes assembly of a second component to the anchor assembly and release of the anchor assembly at the interventional site.

In one particular, non-limiting use in treating incontinence, the elongate tissue access portion 104 of a delivery device is placed within a urethra (UT) leading to a urinary bladder (UB) of a patient. In one approach, the delivery device can be placed within an introducer sheath (not shown) previously positioned in the urethra or alternatively, the delivery device can be inserted directly within the urethra. When employing an introducer sheath, the sheath can be attached to a sheath mount assembly (described below). The patient is positioned in lithotomy. The elongate portion 104 is advanced within the patient until a leading end thereof reaches a target tissue.

Figure 5A:
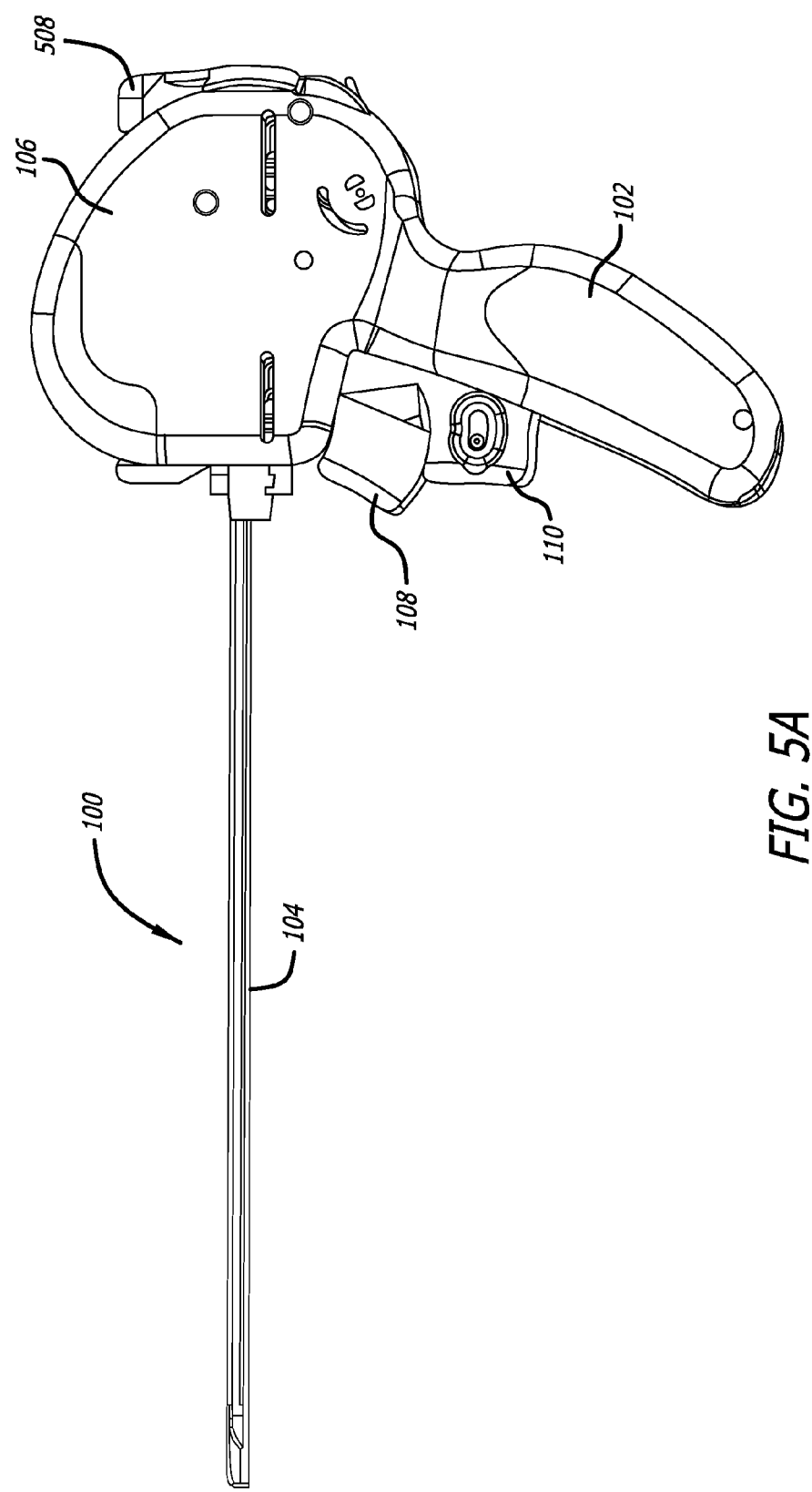
Figure 5B:
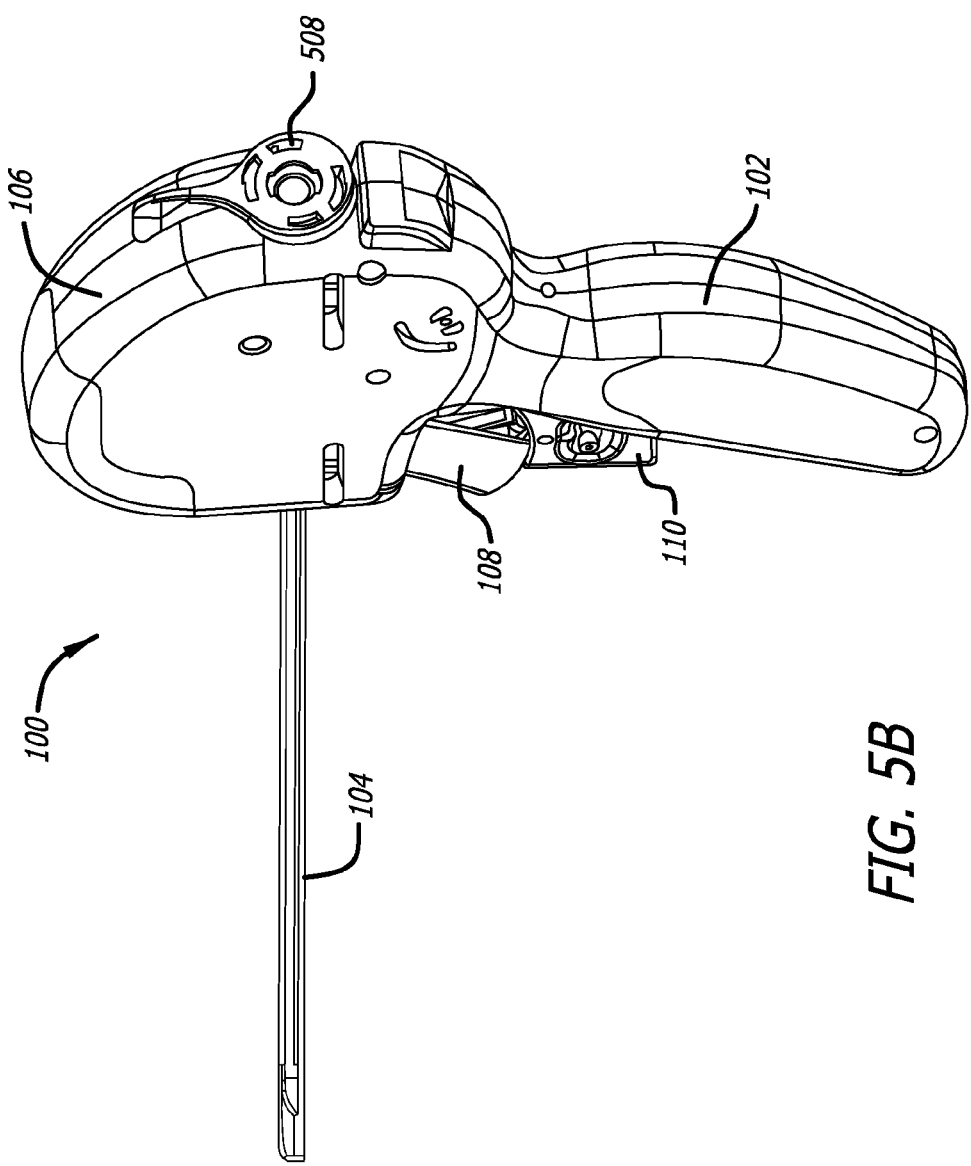

As shown in FIGS. 5A-B, the delivery device is at this stage configured in a ready state. The needle actuator 108 and the needle retracting lever 110 are in an inactivated position.

Figure 5C:
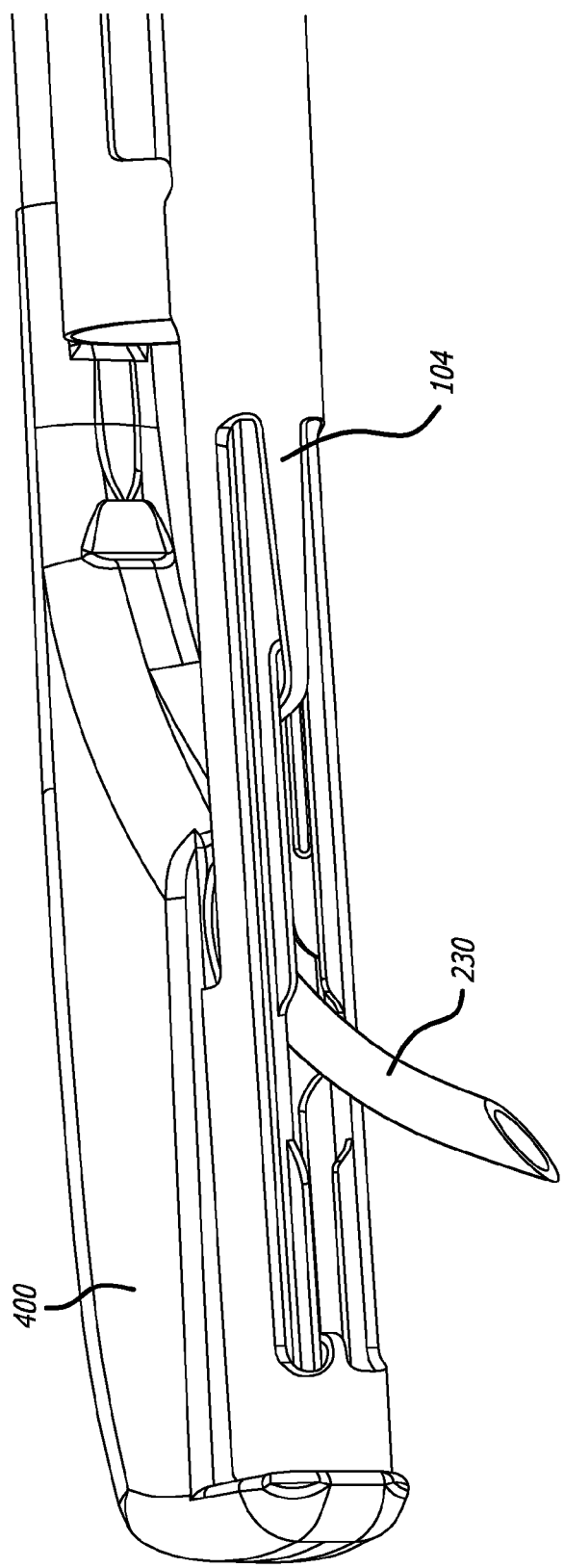

Upon depression of the needle actuator 108, the needle assembly 230 is advanced from within the elongate member 104 (See FIG. 5C). The needle assembly can be configured so that it curves back toward the handle as it is ejected. In use, the needle assembly is advanced through and beyond a target tissue. Spring deployment helps to ensure the needle passes swiftly through the tissue. In one approach, the needle is made from Nitinol tubing and can be coated with Parylene N. Such a coating helps compensate for frictional or environmental losses (e.g., wetness), which may degrade effectiveness of needle penetration.

After complete depression of the needle actuator 108 and the unlocking of the needle retraction lever 110, the needle retraction lever 110 can be actuated. Such action results in a withdrawal of the needle assembly 230, leaving the connector 78 of an anchor assembly in an extended position (See FIG. 5D). In one embodiment, the needle 230 is withdrawn further than its original position within the device pre-deployment.

The proximal anchor actuator assembly 112 is configured at a back end of the casing 106. Actuation of the proximal anchor actuator 112 results in causing the proximal anchor component 84 to engage the connector 78. It also accomplishes cutting a connector 78 to length. Within a patient's body, the anchor assembly is configured across anatomy within the interventional site. The urethra UT is thus stabilized, repositioned or its position is maintained due to the anchor assembly engaging the surrounding tissue. The urethra UT can also be modified using the anchor assemblies, such as by decreasing its size or cross-sectional profile.

Accordingly, an approach involving inserting a tissue suturing or anchoring device into the prostatic urethra UT transurethrally to displace or maintain positioning of the urethra UT is contemplated. The delivery device can also be inserted within the patient's body through an incision site. It is thus contemplated that the anchor delivery device 100 can be advanced through an incision site made in the front of the patient's body, or in the space behind the testicles in the male or through the vagina in a female. An approach originating through the rectum is also contemplated.

As an initial step, sagittal views of a patient's urethra, bladder and surrounding tissues can be taken using transabdominal or transrectal ultrasonography. In this way, the patient's anatomy can be assessed. In this regard, measurements can be taken to determine the various distances and spaces involved in an approach to treat incontinence. After assessing the anatomy, the elongate tissue access assembly 104 of an anchor delivery device (See FIGS. 5A-B) is advanced within the urethra UT or through an incision site.

Next, an anchor assembly can be deployed to stabilize, reposition, modify or hold in place the target urethra UT. As described above, the anchor delivery device accomplishes first deploying a distal anchor 70 and then assembles and attaches a proximal anchor component 84 onto a connector 78. The distal anchor 70 is implanted in anatomy having sufficient purchase. Although the above described tissue anchor matter is shown in a number of drawings relating to treating incontinence, it is to be recognized that various other embodiment of anchors can also be utilized in any of the treatment approaches (See for example, FIG. 10).

As stated, the present disclosure is intended to address all forms of incontinence. In treating Stress Urinary Incontinence (SUI), the fascia and pelvic muscles surrounding the urethra do not adequately hold the urethra UT in position. When intra-abdominal pressure increases, during events such as coughing or sneezing, the urethra can move downward in position, causing urine to leak. In one approach, an anchor assembly 60 including a distal anchor 70 attached to a second anchor 84 by a tensioned suture element 78 is used to stabilize, reposition and hold the urethra UT in the proper position.

Figure 6A:
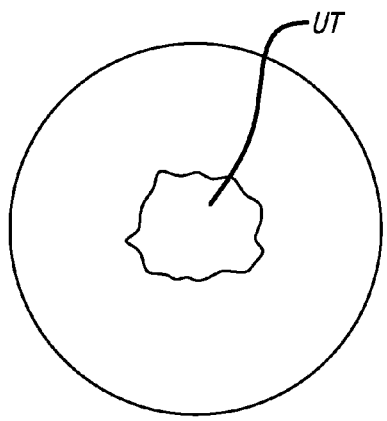
FIGS. 6A-B are cross-sectional views, depicting one incontinence treatment approach.
Figure 6B:
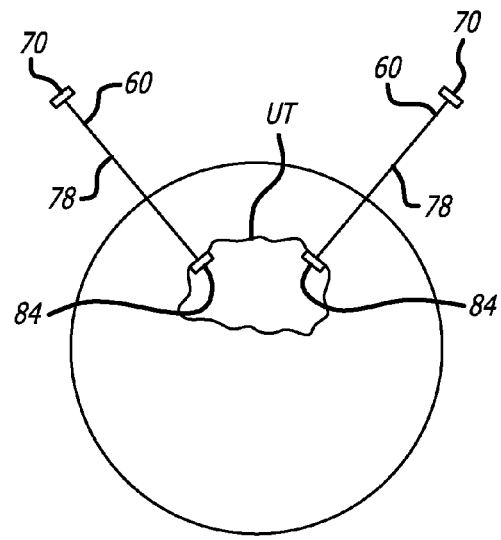

As shown in FIGS. 6A-B in one treatment protocol, the distal anchor 70 is deployed anterior of the urethra UT, the suture 78 is tensioned, and then the proximal anchor 84 would be deployed in the urethra UT. After deployment, the proximal anchor 84 pulls the urethra UT upward based on the tension (FIG. 6A (before) and FIG. 6B (after)).

This approach would provide a treatment that is minimally invasive. The anchor assembly 60 is small and can be delivered transurethrally. The procedure may be performed in the office setting instead of an operating room. Also, side effects and complications from surgery, such as erosion, are reduced. In women, using a conventional sling can result in substantial mesh erosion.

Figure 7:
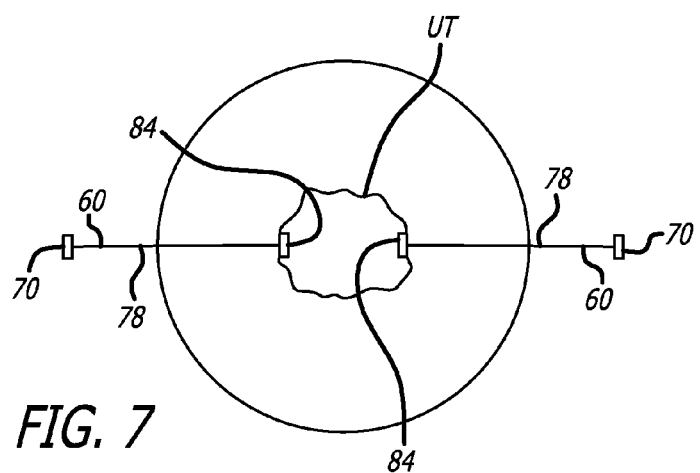
FIG. 7 is a cross-sectional view depicting of another incontinence treatment approach.

In another approach (FIG. 7), the distal anchor 70 can also be deployed laterally relative to the urethra UT. The anchor assembly 60 would tension the urethra UT to stabilize it during increases or changes in intra-abdominal pressure.

Figure 8A:
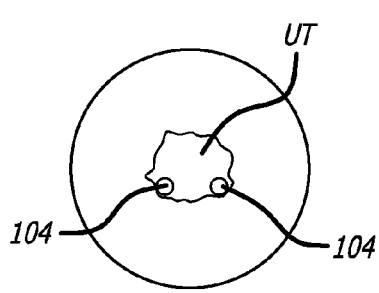
FIGS. 8A-B are cross-sectional views, depicting yet further approaches to treatment.
Figure 8B:
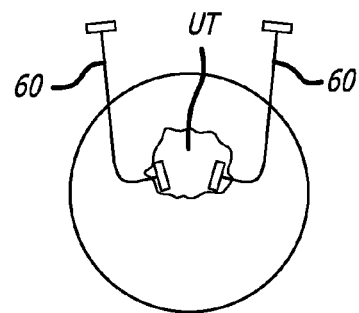

Also, as shown in FIGS. 8A-B, the delivery device 100 could be placed in a low (posterior) position in the urethra UT initially, but the target exterior the urethra UT would be a high (anterior) position. Also, it is contemplated that the delivery device 100 or other instruments can be employed to manipulate tissue to achieve a desired, non-linear trajectory of the connector 60 through tissue defining the urethra UT (See FIG. 8B).

In women, the urethra UT is supported by pelvic floor fascia PFM (See FIG. 3). If this support is insufficient, the urethra UT can move downward at times of increased abdominal pressure leading to urinary incontinence. Devices, which lift the urethra UT towards the abdomen to improve continence, are thus contemplated. In particular, an anchor assembly 60 can be used to treat urinary incontinence by stabilizing, repositioning and/or lifting the urethra UT towards the abdomen, or otherwise stabilize or modify the urethra UT. This can be achieved through several approaches.

Figure 9A:
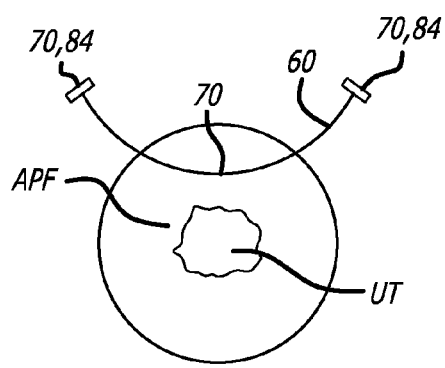
FIGS. 9A-B are cross-sectional views, depicting still further treatment approaches.

In a first approach (FIG. 9A), the connector 78 of an anchor assembly 60 is passed laterally through the anterior periurethral fascia APF and is anchored to lateral tissue or bone. Applying tension along the suture connector 78 would serve to lift the urethra UT towards the abdomen thus reducing incontinence in women in this approach. The suture would not enter the urethral lumen.

Figure 9B:
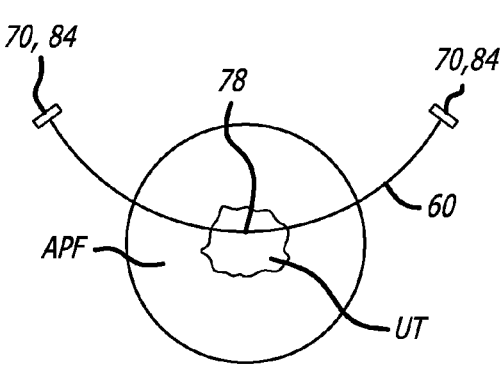

In an alternate approach (FIG. 9B), the connector 78 of an anchor assembly is passed laterally through the anterior periurethral fascia APF and anchored to lateral tissue or bone. Here, the suture connector 78 would pass through the urethral lumen UT. Applying tension along the suture 78 would serve to lift the urethra UT towards the abdomen thus reducing incontinence in women.

Figure 9C:
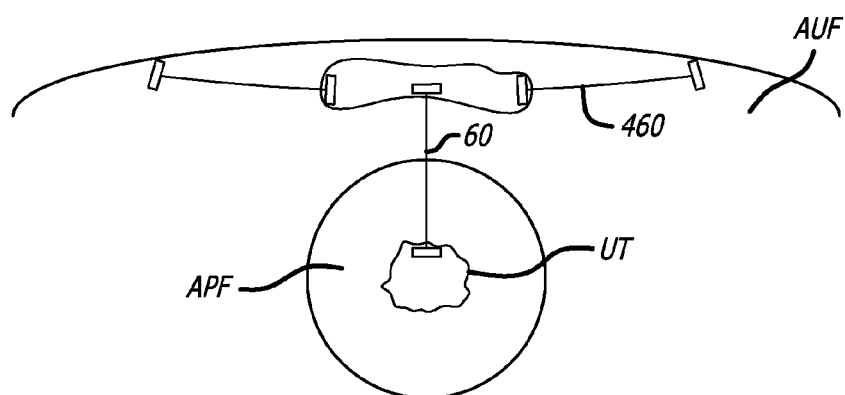
FIG. 9C is a view of a third further treatment approach.

In yet another approach (FIG. 9C), the connector 78 of an anchor assembly 60 is anchored into anterior urethral fascia AUF. Another anchor assembly 60 would serve as a direct link from the fascia to the urethral lumen UT. Applying lateral tension to the sutures lifts the fascia towards the abdomen, which would, in turn, pull the suture connecting the fascia to the urethral lumen UT. As a result, the urethra UT would be pulled towards the abdomen thus reducing incontinence in women. Accordingly, a minimally invasive transurethral or laparoscopic approach is described, one where additional lift or purchase by passing the suture through the urethral lumen UT is suggested or alternatively, in men, the additional lift or purchase is achieved by passing through the prostate capsule.

Figure 10:
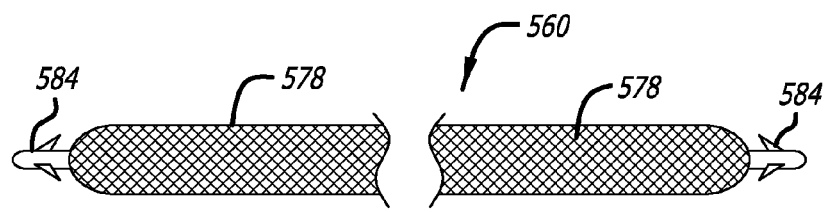
FIG. 10 is a side view, depicting an alternative anchor assembly.

It is also contemplated that incontinence can be treated using a sling device 560 (See FIG. 10). The sling device can include a mid-section defined by an elongate mesh structure 578. At each end of the mesh structure 578 there are extensions including barbs or anchors 584. The sling assembly 560 can be deployed into the prostate PG with both sling ends 584 on the prostate capsule C and with the exposed sling in urethra UT providing tissue stabilizing or repositioning (See FIG. 11). The sling 560 could be initially placed inside a hollow needle or other element and delivered into the tissue via a Trocar. The sling assembly 560 could also be deployed through the prostate, with one sling end on the capsule C and the other sling end residing on the urethra UT to provide tissue repositioning or stabilizing. In a related treatment approach (See FIG. 12), an anchor assembly 60 can be configured across the prostate PG to aid in repositioning or stabilizing of the urethra UT to treat SUI. These approaches to treating urinary incontinence allow for minimally invasive surgical approaches and would be a cost effective, simple way to urinary incontinence.

Figure 11:
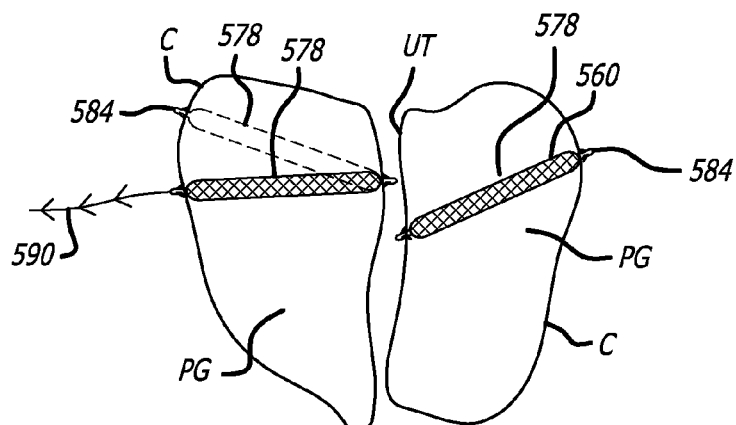
FIG. 11 is a cross-sectional view, depicting use of the structure of FIG. 10 in a treatment approach.

Further, it is contemplated that the sling assembly 560 or anchor assembly 60 can include an anchor having a multi or staged barb component (See 590; FIG. 11) that could provide means for adjustment and custom tissue stabilizing or repositioning. Staged barbs 590 would allow tightening or length adjustment of the sling or anchor assemblies. Also, a wire or similar element could reside in the sling assembly 560 to provide increased column strength. An expandable balloon or other element could reside against the urethra UT to provide adjustable tissue compression. Alternatively, a urethral element can also be used which can twist or rotate to adjust implant length and provide adjustable tissue repositioning or stabilizing.

Figure 12:
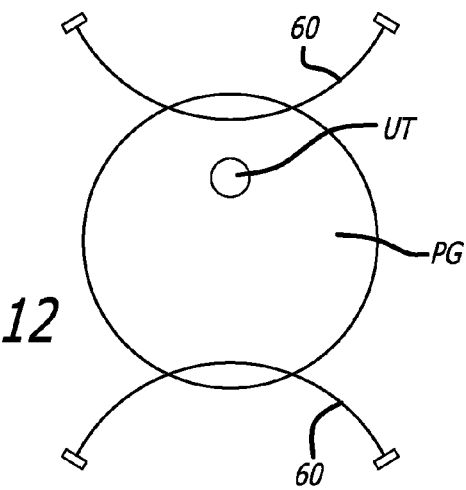
FIG. 12 is a cross-sectional view, depicting a treatment approach involving the prostate.

As shown in FIG. 12, one or more anchor assemblies 60 can be positioned across the prostate PG to treat incontinence. In this approach, the urethra UT is repositioned or stabilized by anchors providing forces on the prostate PG without physical contact with the urethra.

Figure 13A:
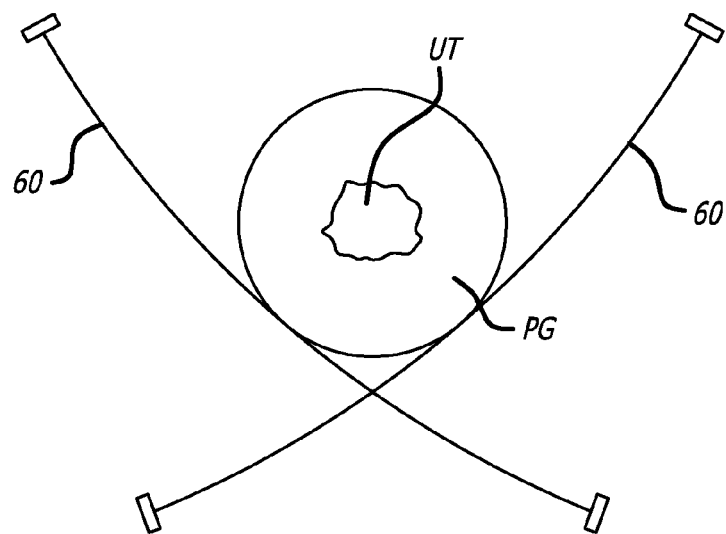
FIGS. 13A-B are cross-sectional views, depicting yet further incontinence treatment approaches.
Figure 13B:
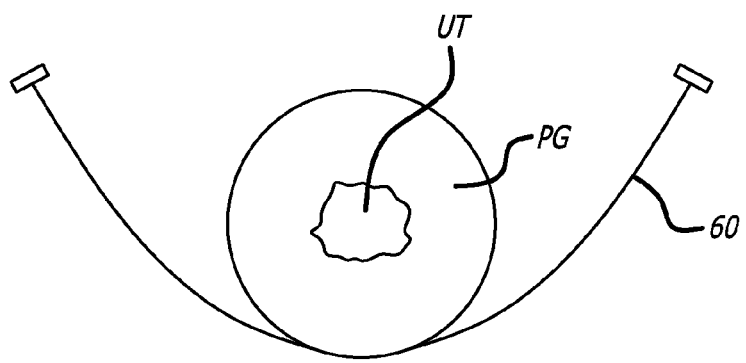
Figure 14A:
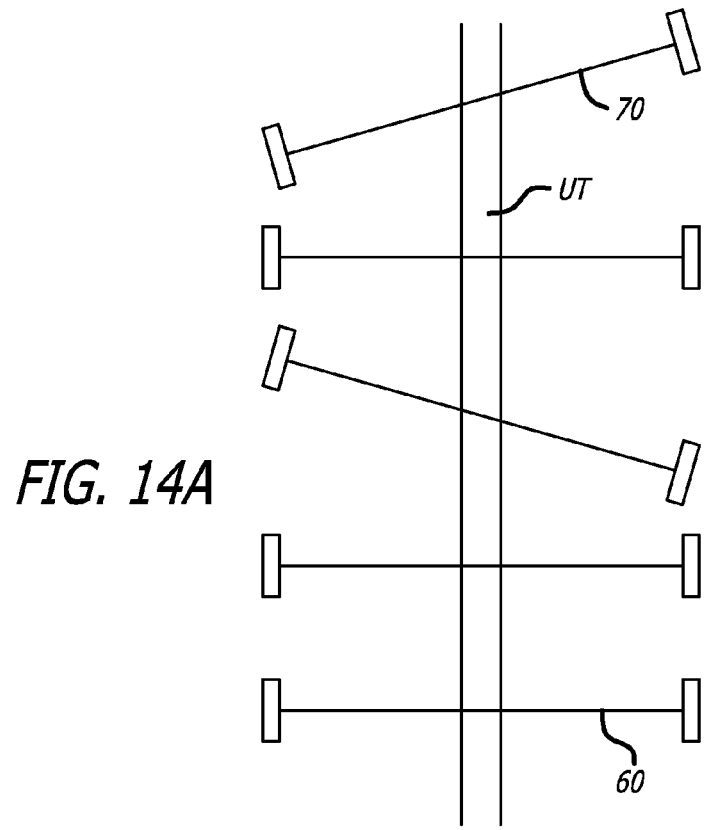
FIGS. 14A-B depict alternative approaches to treatment.
Figure 14B:
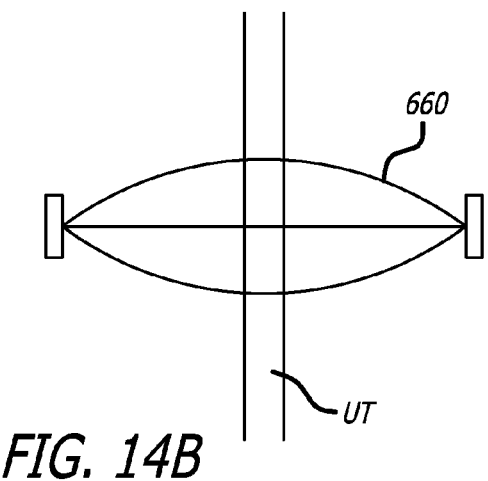

With reference now to FIGS. 13A-B, another approach involves deploying two anchor assemblies 60 in cross-pattern below the prostate PG to hold urethra UT upward in a correct or desired position. Another configuration would be to deploy anchor assembly 60 underneath the prostate PG to hold the urethra UT upward in the desired position (FIG. 13B). Multiple anchor assemblies 60 could also be used along length of urethra UT (FIG. 14A). Alternately, the anchor assembly 660 could be modified from a single monofilament to a multi-strand, splayable suture 678 with shared end connections (FIG. 14B).

It is to be recognized that the approaches depicted in at least FIGS. 6-9 and 13A-B can be utilized in the male treatment of the membranous urethra MU and the bulbous urethra BU (See also FIG. 2). That is, one or more anchor assemblies can be configured through and/or about the membranous and bulbous sections of the urethra UT to reconfigure, stabilize or change the size or shape of these sections of the urethra UT. By so specifically addressing the membranous urethra and bulbous urethra BU, in continence in males can be minimized.

Moreover, it is contemplated that the anchor assembly connector 78 could be replaced with a wider material, such as a biocompatible tape. The connector 78 could also be placed in a diagonal pattern, to provide greater area for the connector to interface with the urethra (See FIG. 14A).

Accordingly, the present invention contemplates both pushing directly on anchor portions of an anchor assembly as well as pushing directly upon the connector of the anchor assembly. Moreover, as presented above, the distal or first anchor component is advanced and deployed through a needle assembly and at least one component of the proximal or second anchor component is advanced and deployed from a housing portion of the anchor deployment device. Further, either a single anchor assembly or multiple anchor assemblies can be delivered and deployed at an intervention site by the deployment device. Additionally, a single anchor assembly component can for example, be placed on one side of a prostate or urethra while multiple anchor assembly components can be positioned along an opposite or displaced position of such anatomy. The number and locations of the anchor assemblies can thus be equal and/or symmetrical, different in number and asymmetrical, or simply asymmetrically placed. Moreover, drug delivery is both contemplated and described as a further remedy in BPH and over active bladder treatment as well as treating prostate cancer and prostatitis.

Once implanted, the anchor assembly of the present invention accomplishes desired tissue manipulation, approximation, compression or retraction as well as cooperates with the target anatomy to provide an atraumatic support structure.

Furthermore, in addition to an intention to cooperate with natural tissue anatomy, the present invention also contemplates approaches to accelerate healing or induce scarring. Manners in which healing can be promoted can include employing abrasive materials, textured connectors, biologics and drugs.

Additionally, it is contemplated that the components of the anchor assembly or selected portions thereof (of any of the anchor assemblies described or contemplated), can be coated or embedded with therapeutic or diagnostic substances (e.g. drugs or therapeutic agents). Again, in the context of treating a prostate gland, the anchor assembly can be coated or imbedded with substances such as 5-alpha-reductase inhibitors, which cause the prostate to decrease in size. Other substances contemplated include but are not limited to phytochemicals generally, alpha-1a-adrenergic receptor blocking agents, smooth muscle relaxants, and agents that inhibit the conversion of testosterone to dihydrotestosterone. In one particular approach, the connector can for example, be coated with a polymer matrix or gel coating, which retains the therapeutic or diagnostic substance and facilitates accomplishing the timed release thereof. Additionally, it is contemplated that bacteriostatic coatings as well as analgesics and antibiotics for prostatitis and other chemical coatings for cancer treatment, can be applied to various portions of the anchor assemblies described herein. Such coatings can have various thicknesses or a specific thickness such that it along with the connector itself matches the profile of a cylindrical portion of an anchor member affixed to the connector. Moreover, the co-delivery of a therapeutic or diagnostic gel or other substances through the implant deployment device or another medical device (i.e. catheter), and moreover an anchor assembly including the same, is within the scope of the present invention as is radio-loading devices (such as a capsular or distal ends of implants for cancer or other treatment modalities). In one such approach, the deployment device includes a reservoir holding the gel substance and through which an anchor device can be advance to pick up a desired quantity of therapeutic or diagnostic gel substance.

It is to be recognized that the timing of the dual advancement of the needle and connector assemblies and subsequent relative motion between the assemblies is coordinated. That is, the needle assembly first provides access to an interventional site and then the connector assembly is left extending beyond a terminal end of the needle assembly through the relative motion of the needle and connector assemblies.

It is further contemplated that in certain embodiments, the anchor delivery device can include the ability to detect forces being applied thereby or other environmental conditions. Various sections of the device can include such devices and in one contemplated approach sensors can be placed along the needle assembly. In this way, an operator can detect for example, whether the needle has breached the target anatomical structure at the interventional site and the extent to which such breaching has occurred. Other sensors, which can detect particular environmental features, can also be employed such as blood or other chemical or constituent sensors. Moreover, one or more pressure sensors or sensors providing feedback on the state of deployment of the anchor assembly during delivery or after implantation are contemplated. For example, tension or depth feedback can be monitored by these sensors. Further, such sensors can be incorporated into the anchor assembly itself, other structure of the deployment device or in the anatomy.

Moreover, it is to be recognized that the foregoing procedure is reversible. In one approach, the connection of an anchor assembly can be severed and a proximal (or second) anchor component removed from the patient's body. For example, the physician can cut the connector and subsequently remove the one or both anchors previously implanted for example, in the patient's urethra.

An aspect that the various embodiments of the present invention provide is the ability to deliver an anchor assembly having a customizable length, each anchor assembly being implanted at a different location without having to remove the device from the patient. Other aspects of the various embodiments of the present invention are load-based delivery, of an anchor assembly, anchor assembly delivery with a device having integrated connector, (e.g. suture), cutting, and anchor assembly delivery with an endoscope in the device. The delivery device is uniquely configured to hold the suture with tension during delivery to help ensure that the first anchor component sits firmly against a tissue plane (e.g., the outer capsule of the prostate) and is held relatively firm as the second anchor component is attached to the connector and the delivery device. In this aspect, the needle assembly acting as a penetrating member is cooperatively connected to a mechanism, which pulls on the anchor while the needle assembly is retracted.

It is to be recognized that various materials are within the scope of the present invention for manufacturing the disclosed devices. Moreover, one or more components such as distal anchor, proximal anchor, and connector, of the one or more anchor devices disclosed herein can be completely or partially biodegradable or biofragmentable.

Further, as stated, the devices and methods disclosed herein can be used to treat a variety of pathologies in a variety of lumens or organs comprising a cavity or a wall. Examples of such lumens or organs include, but are not limited to urethra, bowel, stomach, esophagus, trachea, bronchii, bronchial passageways, veins (e.g. for treating varicose veins or valvular insufficiency), arteries, lymphatic vessels, ureters, bladder, cardiac atria or ventricles, uterus, fallopian tubes, etc.

Finally, it is to be appreciated that the invention has been described herein with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unpatentable or unsuitable for its intended use. Also, for example, where the steps of a method are described or listed in a particular order, the order of such steps may be changed unless to do so would render the method unpatentable or unsuitable for its intended use. All reasonable additions, deletions, modifications and alterations are to be considered equivalents of the described examples and embodiments and are to be included within the scope of the following claims.

Thus, it will be apparent from the foregoing that, while particular forms of the invention have been illustrated and described, various modifications can be made without parting from the spirit and scope of the invention.

What is claimed is:

1. A method for treating incontinence, comprising:
   implanting a first anchor;
   implanting a second anchor with a connector between the first and second anchors, wherein the first anchor, second anchor, and connector are implanted exterior to a prostate gland;
   connecting the first anchor, second anchor, and connector to define a first anchor assembly; and
   stabilizing a position of the urethra without maintaining compression on prostatic tissue during the time the position of the urethra is stabilized.

2. The method of claim 1, further comprising inserting an anchor delivery device within a urethral lumen and actuating the anchor delivery device.

3. The method of claim 1, wherein stabilizing a position of the urethra comprises repositioning then stabilizing the position of the urethra.

4. The method of claim 1, wherein stabilizing a position of the urethra comprises stabilizing the position of the urethra without repositioning the urethra.

5. The method of claim 4, wherein connecting the first anchor, second anchor, and connector to define a first anchor assembly provides lateral forces to the urethra to offset changes in intra-abdominal pressures in the urethra to treat incontinence.

6. The method of claim 1, further comprising configuring the connector through anterior periurethral fascia.

7. The method of claim 1, further comprising configuring the first anchor assembly and a second anchor assembly such that connectors thereof are positioned against a prostate capsule.

8. The method of claim 7, wherein the connectors of the first and second anchor assemblies cross.

9. The method of claim 1, further comprising placing a plurality of anchor assemblies spaced along a longitudinal length of the urethra.

10. The method of claim 1, further comprising assembling the anchor assembly in situ.

11. The method of claim 10, wherein the anchor assembly has a length, further comprising determining the length in situ.

12. The method of claim 1, further comprising configuring the connector so that upon implantation the connector assumes a non-linear trajectory through the tissue defining the urethra.

\* \* \* \* \*